US006468798B1

(12) United States Patent
Debs et al.

(10) Patent No.: US 6,468,798 B1
(45) Date of Patent: *Oct. 22, 2002

(54) EXPRESSION OF CLONED GENES IN THE LUNG BY AEROSOL AND LIPOSOME-BASED DELIVERY

(75) Inventors: Robert James Debs, Mill Valley; Ning Zhu, San Francisco, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 16 days.

(21) Appl. No.: 09/006,841

(22) Filed: Jan. 14, 1998

Related U.S. Application Data

(63) Continuation of application No. 07/972,135, filed on Nov. 5, 1992, now Pat. No. 5,858,784, which is a continuation-in-part of application No. 07/809,291, filed on Dec. 17, 1991, now abandoned.

(51) Int. Cl.⁷ .......................... A61K 9/127; C12N 15/00
(52) U.S. Cl. ....................... 435/458; 435/455; 424/450
(58) Field of Search ........................... 424/450; 435/6, 435/69.1, 91.1, 440, 455, 458, 325, 354, 366, 371, 375, 320.1; 536/23.1, 23.5, 24.31, 24.5

(56) References Cited

U.S. PATENT DOCUMENTS

| | | | |
|---|---|---|---|
| 3,826,255 A | 7/1974 | Havstad et al. | 128/200.18 |
| 4,046,146 A | 9/1977 | Rosskamp et al. | 128/203.15 |
| 4,253,468 A | 3/1981 | Lehmbeck | 600/539 |
| 4,268,460 A | 5/1981 | Boiarski et al. | 261/1 |
| 4,394,448 A | 7/1983 | Szoka et al. | 435/458 |
| 4,510,929 A | 4/1985 | Bordoni et al. | 128/200.14 |
| 4,649,911 A | 3/1987 | Knight et al. | 128/200.21 |
| 4,804,678 A | 2/1989 | Augstein et al. | 514/456 |
| 4,946,787 A | * 8/1990 | Eppstein et al. | 264/4.1 |
| 5,032,407 A | 7/1991 | Wagner | 800/23 |
| 5,049,386 A | 9/1991 | Eppstein | 424/427 |
| 5,075,229 A | 12/1991 | Hanson | 514/44 |
| 5,240,842 A | 8/1993 | Mets | 435/470 |
| 5,240,846 A | * 8/1993 | Collins et al. | 435/371 |
| 5,264,618 A | * 11/1993 | Felgner et al. | 560/224 |
| 5,279,833 A | 1/1994 | Rose | 424/450 |
| 5,641,662 A | * 6/1997 | Debs et al. | 435/458 |
| 5,676,954 A | 10/1997 | Brigham | 424/450 |
| 5,858,784 A | * 1/1999 | Debs et al. | 435/375 |

FOREIGN PATENT DOCUMENTS

| | | |
|---|---|---|
| DE | 3545126 | 6/1987 |
| EP | 0 281 246 A2 | 9/1988 |
| EP | 0 466 017 A1 | 9/1991 |
| EP | 0 469 632 A1 | 2/1992 |
| GB | 354126 | 8/1931 |
| WO | WO 89/02469 | 3/1989 |
| WO | WO 89/12109 | 12/1989 |
| WO | WO 90/12878 | 1/1990 |
| WO | WO 90/01515 | 2/1990 |
| WO | WO 90/06997 | 6/1990 |
| WO | WO 90/10448 | 9/1990 |
| WO | WO/90/11092 | 10/1990 |
| WO | WO 91/02796 | 3/1991 |
| WO | WO 91/06309 | 5/1991 |
| WO | WO 91/15501 | 10/1991 |
| WO | WO 91/17773 | 11/1991 |
| WO | WO 92/05252 | 4/1992 |
| WO | WO 92/05273 | 4/1992 |
| WO | WO 92/19749 | 11/1992 |
| WO | WO 93/04701 | 3/1993 |
| WO | WO 93/12240 | 6/1993 |
| WO | WO 93/12756 | * 7/1993 |
| WO | WO 93/24640 | 12/1993 |

OTHER PUBLICATIONS

Dzau, Victor J., et al. (1993) "Gene therapy for cardiovascular disease", TIBTECH 11:205–210.

Friedmann, Theodore (1989) "Progress Toward Human Gene Therapy", Science 244:1275–1281.

Zhu, Ning, et al., (1993) "Systemic Gene Expression After Intravenous DNA Delivery into Adult Mice", Science, 261:209–211.

Rosenfeld, et al. (1992) "In vivo Transfer of the Human Cystic Fibrosis Transmembrane Conductance Regulator Gene to the Airway Epithelium", Cell, 68:143–155.

Alton, E., et al. (1993) "Non–invasive liposome–mediated gene delivery can correct the ion transport defect in cyctic fibrosis mutant mice", Nature Genetics, 5:135–142.

Papahadjoupoulos, et al., (1975), "Chochleate Lipid Cylinders: Formation by Fusion of Unilamellar Lipid Vesicles," Biochimica et Biophysica Acta, 394:483–491.

Deamer et al., (1976), "Large Volume Liposomes by an Ether Vaporization Method", Biochimica et Biophysica Acta, 443:629–634.

Ostro, et al., (1977), "Incorporation of High Molecular Weight RNA into large Artificial Lipid Vesicles", Biochemical and Biophysical Research Communications, 76(3):836–842.

(List continued on next page.)

Primary Examiner—Sean McGarry
Assistant Examiner—Janet L. Epps
(74) Attorney, Agent, or Firm—Townsend & Townsend & Crew LLP

(57) ABSTRACT

Methods and compositions for producing a mammal capable of expressing an exogenously supplied gene in cells of the airway are disclosed. Liposome-nucleic acid complexes are prepared then delivered via aerosol to the lung airway. The invention provides a direct method for transforming pulmonary cells, treat disorders of the lung, and for delivering substances systematically following expression in the lung.

38 Claims, 20 Drawing Sheets

OTHER PUBLICATIONS

Enoch, et al., (1979) "Formation and Properties of 1000–.ANG.–Diameter, Single–Bilayer Phospholipid Vesicles", PNAS (USA), 76(1):145–149.

Wilson et al., (1979) "The Introduction of Poliovirus RNA into Cells via Lipid Vesicles (Lipsomes)", Cell, 17:77–84.

Fraley, et al., (1979) "Entrapment of a Bacterial Plasmid in Phospholipid Vesicles: Potential for Gene Transfer", PNAS (USA), 76(7):3348–3352.

Leserman, et al., (1980) "Targeting to Cells of Fluorescent Liposomes Covalently Coupled with Monoclonal Antibody or Protein A", Nature, 288:602–604.

Beaucage, et al., (1981) "Deoxynucleoside Phosphoramidites—A New Class of Key Intermediates for Deoxypolynucleotide Synthesis", Tetrahedron Letters, 22(20):1859–1862.

Duckworth, et al. (1981) "Rapid Synthesis of Oligodeoxyribonucleotides VI. Efficient, Mechanised Synthesis of Heptadecadeoxyribonucleotides by an Improved Solid Phase Phosphotriester Route", Nucleic Acids Research, 9(7):1691–1706.

Martin, et al. (1981) "Immunospecific Targeting of Liposomes to Cells: A Novel and Efficient Method for Covalent Attachment of Fab' Fragments via Disulfide Bonds", Biochemistry, 20:4229–4238.

Matteucci, et al. (1981) "Synthesis of Deoxyoligonucleotides on a Polymer Support," J. Am. Chem. Soc., 103:3185–3191.

Volloch, et al. (1981) "Stability of Globin mRNA in Terminally Differentiating Murine Erythroleukemia Cells," Cell, 23:509–514.

Bothwell, et al. (1981) "Heavy Chain Variable Region Contribution to the NP.sup.b Family of Antibodies: Somatic Mutation Evident in .gamma.2a Variable Region," Cell, 24:625–637.

Edge, et al. (1981) "Total Synthesis of a Human Leukocyte Interferon Gene," Nature, 292:756–762.

Schaefer–Ridder, et al. (1981) "Liposomes as Gene Carriers: Efficient Transformation of Mouse L Cells by Thymidine Kinase Gene," Science, 215(8):166–168.

Gorman, et al. (1982) "Recombinant Genomes which Express Chloramphenicol Acetyltransferase in Mammalian Cells," Molecular and Cellular Biology 2(2):1044–1051.

Gorman, et al. (1982) "The Rous Sarcoma Virus Long Terminal Repeat is a Strong Promoter when Introduced into a Variety of Eukaryotic Cells by DNA–Mediated Transfection," PNAS (USA), 79:6777–6781.

Long, et al. (1984) "Complete Sequence of the cDNA for Human .alpha..sub.1 –Antitrypsin and the Gene for the S Varient," Biochemistry, 23:4828–4837.

Nambiar, et al. (1984) "Total Synthesis and Cloning of a Gene Coding for the Ribonuclease S. Protein," Science 223:1299–1301.

Jay, et al. (1984) "Chemical Synthesis of a Biologically Active Gene for Human Immune Interferon–.gamma.," Journal of Biological Chemistry, 259(10):6311–6317.

Kunkel, Thomas (1985) "Rapid and efficient site–specific mutagenesis without phenotypic selection," PNAS (USA), 82:488–492.

Boshart, et al. (1985) "A very Strong Enhancer is Located Upstream of an Immediate Early Gene of Human Cytomegalovirus," Cell, 41:521–530.

Stinski, et al. (1985) "Activation of the Major Immediate Early Gene of Human Cytomegalovirus by cis–Acting Elements in the Promoter–Regulatory Sequence and by Virus–specific trans–acting Components," Journal of Virology, 55(2):431–441.

Cullen, B.R. (1986) "Trans–Activation of Human Immunodeficiency Virus Occurs via a Bimodal Mechanism," Cell, 46:973–982.

Benvenisty, et al. (1986) "Direct introduction of genes into rats and expression of the genes," PNAS (USA), 83:9551–9555.

Wang, et al. (1987) "pH Sensitive Immunoliposomes Mediate Target–Cell–Specific Delivery and Controlled Expression of a Foreign Gene in a Mouse," PNAS (USA), 84:7851–7855.

Sakai, et al. (1988) "Hormone–Mediated Repression: A Negative Glucocorticoid Response Element from the Bovine Prolactin Gene," Genes and Development, 2:1144–1154.

Stamatatos, et al. (1988) "Interactions for Cationic Lipid Vesicles with Negatively Charged Phospholipid Vesicles and Biological Membranes", Biochemistry, 27:3917–3925.

Wu, et al. (1988) "Receptor–Mediated Gene Delivery and Expression In Vivo," J. Biological Chemistry, 263(29):14621–14624.

Kaneda, et al. (1989) "Increased Expression of DNA Cointroduced with Nuclear Protein in Adult Rat Liver," Science 243:375–378.

Rommens, et al. (1989) "Identification of the Cystic Fibrosis Gene: Chromosome Walking and Jumping," Science, 245:1059–1065.

Goodfellow, P.N. (1989) "Steady Steps Lead to the Gene," Nature, 341:102–103.

Mizuno, et al. (1989) "In Vitro and In Vivo Expression of Human Interferon–.beta. in Glioma Cells Transfected with its Gene Encapsulated in Liposomes," J. Interferon Research, 9, Supp. 2:S151 (Abstract A1–8).

Huang, et al. (1990) "Intervening Sequences Increase Efficiency of RNA 3' Processing and Accumulation of Cytoplasmic RNA," Nucleic Acids Research, 18(4):937–947.

Ono, et al. (1990) "Plasmid DNAs Directly Injected into Mouse Brain with Lipofectin Can Be Incorporated and Expressed by Brain Cells," Neuroscience Letters, 117:259–263.

Holt, et al. (1990) "Lipofection of cDNAs in the Embryonic Vertebrate Central Nerous System," Neuron, 4:203–214.

Uhlman, et al. (1990) "Antisense Oligonucleotides: A New Therapeutic Principle," Chemical Reviews, 90(4):543–584.

Crystal, R.G. (1990) ".alpha.1–Antitrypsin Deficiency, Emphysema, and Liver Disease", The Journal of Clinical Investigation, Inc., 85:1343–1352.

Shyu, Ann–Bin, et al. (1989) "The c–fos transcript is targeted for rapid decay by two distinct mRNA degradation pathways", Genes & Development, 3:60–72.

Rosenberg, et al. (1990) "Gene Transfer into Humans—Immunotherapy of Patients with Advanced Melanoma, Using Tumor–Infiltrating Lymphocytes Modified by Retrovital Gene Transduction", The New England Journal of Medicine, 323(9):570–578.

Burhans, et al. (1990) "Identification of an Origin of Bidirectional DNA Replication in Mammalian Chromosomes", Cell. 62:955–965.

Verma (1990) "Gene Therapy: Treatment of disease by introducing heathy genes into the body is becoming feasible. But the therapy will not reach its full potential until the genes can be coaxed to work throughout life", Scientific American, 68–84.

Barr, et al. (1991) "Expression of Recombinant Genes in Myocardium In Vivo Following Direct Injection of DNA", Clinical Research, 39:2:152A.

Kitsis, et al. (1991) "Behaviour of Genes Directly Transferred to Rat Heart In Vivo", Clinical Research, 39:2:152A.

Palmiter, et al. (1991) "Heterologous introns can enhance expression of transgenes in mice," PNAS (USA), 88:478–482.

Felgner, et al. (1991) "Gene Therapeutics", Nature, 349:351–352.

Weatherall, D.J. (1991) "Gene Therapeutics", Nature, 349:275–276.

Fleischman, Roger A. (1991) Southwestern Internal Medicine Conference: Human Gene Therapy, The American Journal of the Medical Sciences, 301(5):353–363.

Kitsis, et al. (1991) "Hormonal Modulation of a Gene Injected into Rat Heart In Vivo", PNAS (USA), 88:4138–4142.

Choi, et al. (1991) "A Generic Intron Increases Gene Expression in Transgenic Mice", Molecular and Cellular Biology, 11(6);3070–3074.

Lim, et al. (1991) "Direct In Vivo Gene Transfer into the Coronary and Peripheral Vasculatures of the Intact Dog", Circulation, 83(6):2007–2001.

Wu, et al. (1991) "Receptor–Mediated Gene Delivery In Vivo", Journal of Biological Chemistry, 266(22):14338–14342.

Ascadi, et al. (1991) "Human Dystrophin Expression in mdx Mice after Intramuscular Injection of DNA Constructs", Nature, 352:815–818.

Rosenberg (1991) "Immunotherapy and Gene Therapy of Cancer", Cancer Research (Supp.), 51(18):5074S–5079S.

Anderson, W. French (1992) "Human Gene Therapy", Science 256:808–813.

Collins, Francis S. (1992), "Cystic Fibrosis: Molecular Biology and Therapeutic Implications", Science, 256:774–783.

Cox, et al. (1988) "Emphysema of Early Onset Associated with a Complete Deficiency of Alpha–1–Antitrypsin (null homozygotes).sup.1–3", Am. Rev. Respir. Dis., 137:371–375.

Maxam, et al. (1980) "Sequencing End–Labeled DNA with Base–Specific Chemical Cleavages", Methods in Enzymology, 65:499–560.

Wright, B.M. (1958) "A New Nebuliser", Lancet, 2:24–25.

Raabe, Otto G. (1971) "Particle Size Analysis Utilizing Group Data and the Log–Normal Distribution", J. Aerosol Sci., 2:289–303.

Szoka, et al. (1978) "Procedure for preparation of liposomes with large internal aqueous space and high capture by reverse–phase evaporation", PNAS (USA), 75(9):4194–4198.

Dobbs, et al. (1986) "An Improved method for isolating Type II cells in High Yield and Purity.sup.1–3", Amer. Rev. Respiratory Disease, 134:141–145.

Debs, et al (1986) "Selective Enhancement of Pentamidine Uptake in the Lung by Aerosolization and Delivery in Liposomes", Amer. Rev. Respiratory Disease, 135:731–737.

Lai, et al. (1988), "The essential role of microsomal deacetylase activity in the metabolic activation, DNA–(deoxyguanosin–8–yl)–2–aminofluorene adduct formation and initiation of liver tumors by N–hydroxy–2–acetylaminoflurorene in the livers of infant male B6C3F.sub.1 mice", Carginogenesis, 9:1295–1302.

Beardsley, et al. (1989) "Winning Candidate: A pair staking search identifies the gene for cystic fibrosis", Sci. Am., 261:28–30.

Treat, et al. (1990) "Antitumor activity of liposome–encapsulated doxorubicin in advanced breast cancer Phase II study", J. Natl. Cancer Institut., 82:1706.

Rasmussen. O.F. (1991) "Listeria monocytogenes can be classified into two major types according to the sequence of the listeriolyson gene", Infect. and Immun., 59(11):3945–3951.

Marino, et al. (1991) "Localization of the Cystic Fibrosis Transmembrane Conductance Regulator in Pancreas", J. Clin. Invest., 88:712–716.

Chou, et al. (1991) "Characterization in the Promoter Region of the Cystic Fibrosis Transmembrane Conductance Regulator Gene", The Journal of Biological Chemistry 266:24471–24476.

Trezise, et al. (1991) "In Vivo Cell–Specific Expression of the Cystic Transmembrane Conductance Regulator," Nature, 353:434–437.

Brinster, et al. (1988) "Introns Increase Transcriptional Efficiency in Transgenic Mice", Proc. Natl. Acad. Sci. USA, 85:836–840.

Debs, et al. (1991) "Prolonged Transgene Expression in Rodent Lung Cells", Am. J. Respir. Cell Mol. Biol., 7:406–413.

Drumm, et al. (1990) "Correction of the Cystic Fibrosis Defect In Vitro by Retrovirus–Mediated Gene Transfer", Cell, 62:1227–1233.

Gregory, et al. (1990) "Expression and Characterization of the Cystic Fibrosis Transmembrane Conductance Regulator," Nature, 347:382–386.

Nicolau, et al. (1983) "In Vivo Expression of Rat Insulin After Intravenous Administration of the Liposome–Entrapped Gene for Rat Insulin I", Proc. Natl. Acad. Sci. USA, 80:1068–1072.

Rich, et al. (1990) "Expression of Cystic Fibrosis Transmembrane Conductance Regulator Corrects Defective Chloride Channel Regulation in Cystic Fibrosis Airway Epithelial Cells", Nature, 347:358–363.

Riordan, et al. (1989), "Identification of the Cystic Fibrosis Gene: Cloning and Characterization of Complementary DNA", Science, 245:1066–1073.

Stribling, et al. (1992) "The Mouse as a Model for Cationic Lipsome–Based Aerosolized Gene Delivery", Journal of Biopharmaceutical Science, 3(1/2) 255–263.

Taylor, et al. (1993) "Liposomes for Drug Delivery to the Respiratory Tract", Drug Development and Industrial Pharmacy, 19(1/2), 123–142.

Rosenfeld, et al., "Adenovirus–Mediated Transfer of a Recombinant .alpha.1–Antitrypsin Gene to the Lung Epithelium in Vivo", Science 252:431–434 (1991).

Felgner, et al., "Lipofection: A Highly Efficient, Lipid–Mediated DNA–Transfection Procedure," PNAS (USA), vol. 84:7413–7417 (1987).

Mannino, et al., "Liposome Mediated Gene Transfer," Biotechniques, vol. 6 No. 7:682–690 (1988).

Hubbard, et al., "Fate of Aerosolized Recombinant DNA–Produced .alpha.1–Antitrypsin: Use of the Epithelial Surface of the Lower Respiratory Tract to Administer Proteins of Therapeutic Importance," PNAS (USA) vol. 86:680–684 (1989).

Malone, et al., "Cationic Liposome–Mediated RNA Transfection," PNAS (USA), vol. 86:6077–6081 (1989).

Hug, et al., "Liposomes for the Transformation of Eukaryotic Cells", Biochemica et Biophysica Acta, 1097:1–17 (1991).

Debs, et al., "Biodistribution, tissue reaction and lung retention of Pentamidine aerosolized as three different salts," Am. Rev. Respir. Dis., 142:1164–1167 (1990).

Canonico, et al., "Expression of a CMV promoter driven human .alpha.–1 antitrypsin gene in cultured lung endothelial cells and in the lungs of rabbits", Clinical Research, 39:219A (1991).

Hazinski, et al., Am. J. Respir. Cell. Mol. Biol. (1991) 4:206–209.

Brigham, et al., Am. J. Med. Sci. (1989) 289:278–281.

Wolff, et al., Science (1990) 247: 1465–1468.

Nabel, et al., Science (1990) 249: 1285–1288.

Debs, et al., Antimicrob. Agents Chemother. 31:37–41 (1987).

Debs., et al., Amer. Rev. Respir. Dis., 135:731–737 (1987).

Debs, et al.. J. Immunol., 140:3482–3488 (1988).

Montgomery, et al., Lancet, 11:480–483 (1987).

Montgomery, et al., Chest, 95:747–751 (1989).

Leoung, et al., N. Eng. J. Med., 323:769–775 (1990).

Gregoriadis, Trends in Biotechnology, 3(9):235–241 (1985).

Straubinger, et al. Meth. Enzymol., 101:512–527 (1983).

Holden, et al., Science, 253:964–965 (1991).

Huang, et al., Molecular and Cellular Biology, 10(4):1805–1810 (1990).

Brigham et al., (1989) "Expression of a Prokaryotic Gene in Cultured Lung Endothelial Cells after Lipofection with a Plasmid Vector" Am. J. Respir. Cell. Mol. Biol. 1:95–100.

A. Miller, Nature 357:455–60 (1992).

N. Dillon, TIBTECH, 11:167–73 (1993).

S. Hyde et al. Nature 362 (Mar. 18, 1993) 250–5.

H. San et al. Human Gene Therapy 4:781–788 (1993).

L. Schwarz et al. Human Gene Therapy 7:731–41 (1996).

R. Stribling et al. PNAS 82:11277–81 (1992).

X. Gao et al. BBRC 179(1):280–5 (1991).

K. Yoshimura et al. NAR 20(12):3233–40 (1992).

D. Porteous et al., TIBTECH 11:173–81 (1993).

J. Van Brumt et al. Biotechnology 6(10)1149–54 (1988).

* cited by examiner

HCMV (Towne) -> Full Restriction Map                                                                      (SEQ ID NO:1)

DNA sequence   616 b.p.   ggcgaccgccca ... agtgacgtaagt    linear

Positions of Restriction Endonucleases sites (unique sites underlined)

```
                     Mae II
                     Aha II                             Mae III
                     Aat II         Mae III              |                                              Nde I
             HinC II  |   Mae II     |                   |                     Bgl I     Rsa I           |
              |  |    |    |         |                   |                       |         |             |
              26 29  29   39        42                  57                     114       126           141
              |   |   |   ||         |                   |                       |         |             |
              |   |   |   ||         |                   |                       |         |             |
GGCGACCGCCCAGCGACGACCCCGCCCGTTGACGTCAATAGTGACGTATGTTCCCATAGTAACGCCAATAGGGACTTTCCAT   80
CCGCTGGCGGGTCGCTGCTGGGGCGGGCAACTGCAGTTATCACTGCATACAAGGGTATCATTGCGGTTATCCCTGAAAGGTA

Mae II
    Aha II
    Aat II
    | | |
    | | |
TGACGTCAATGGGTGGAGTATTTACGGTAAACTGCCCACTTGGCACATCAAGTGTATCATATGCCAAGTCCGCCCCC  160
ACTGCAGTTACCCACCTCATAAATGCCATTTGACGGGTGAACCGTCAGTTCACATAGTATACGGTTCAGGCGGGGG
82  82
82  82
83
```

FIG. 6A(1)

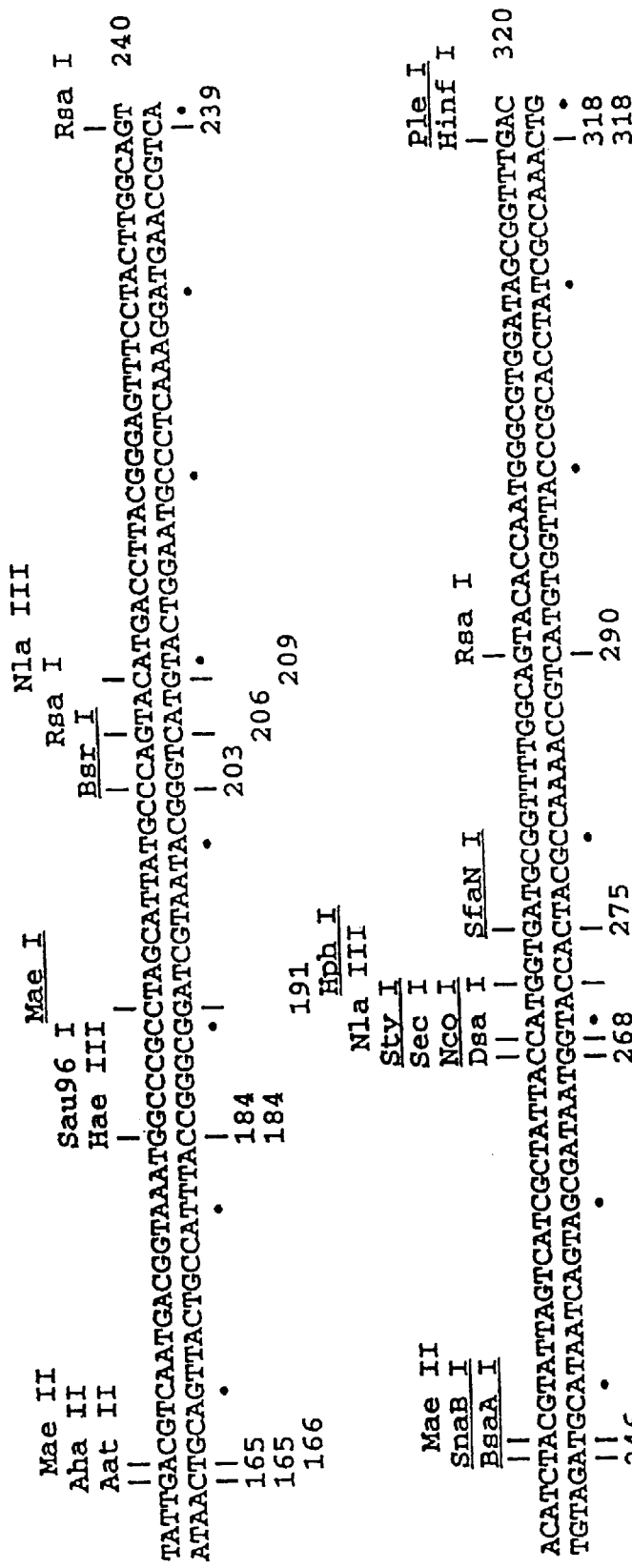
FIG. 6A(2)

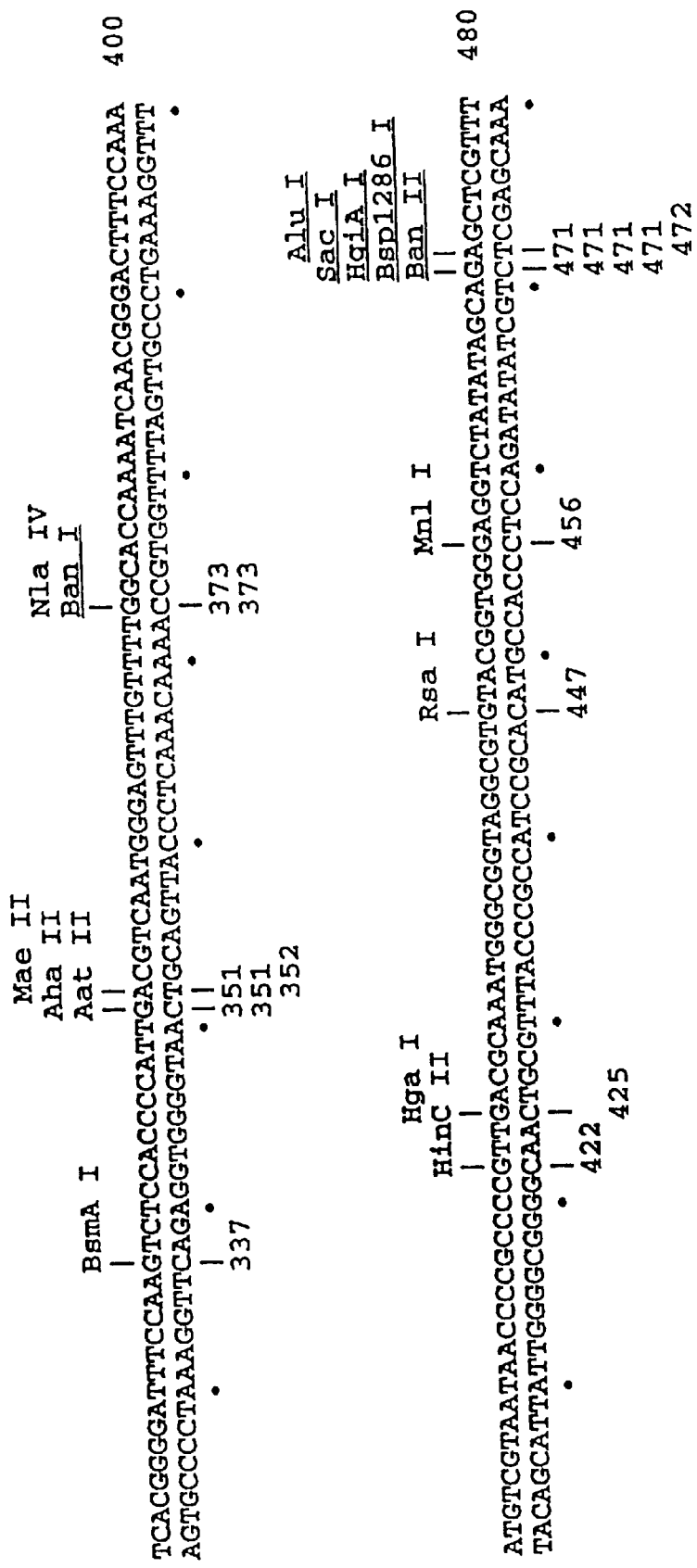
FIG. 6A(3)

FIG. 6A(4)

```
*** Aligned sequences:
C1 ( 1f): |>u 1>+++++ ad169hcmv  (930 bases)+++++>u 930>|
C2 ( 1f): |>u 1>+++++ hs5miel    (616 bases)+++++>u 616>|

*** Alignment of first sequence with all others displayed
*** Key:
    UPPER CASE = aligned non-identical bases
    lower case = unaligned bases
    ---------- = aligned identical bases
    .......... = gap
```

(SEQ ID NO:2)
(SEQ ID NO:3)

```
ad169hcmv : AATCAATATTGGCCATTAGCCATATTATTCATTGGTTTATATAGCATAAATCAATATTGGC
hs5miel   : ............................................................

ad169hcmv : TATTGGCCATTGCATACGTTGTATCCATATCATAATCATAATATGTACATTTATATTGGCTCATGT
hs5miel   : ............................................................

ad169hcmv : CCAACATTACCGGCCATGTTGACATTGATTATTGACTAGTTATTAATAGTAATCAATTACG
hs5miel   : ............................................................

ad169hcmv : GGGTCATTAGTTCATAGCCATATATGGAGTTCCGCGTTACATAACTTACGGTAAATGGC
hs5miel   : ............................................................

ad169hcmv : CCGCCTGGCTGACCGCCCAACGACCCCCGCCCATTGACGTCAATAATGACGTATGTTCCC
hs5miel   : ...........-------------G----------------------G---------- ad169hcmv : ATAGTAACGCCAATAGGGACTTTCCATTGACGTCAATGGGTGGAGTATTTACGGTAAACT
hs5miel   : ------------------------------------------------------------
```

FIG. 6B(1)

```
ad169hcmv : GCCCACTTGGCAGTACATCAAGTGTATCATATGCCAAGTACGCCCCCTATTGACGTCAAT
hs5mie1   : ------------------------------------------C----------------- ad169hcmv : GACGGTAAATGGCCCGCCTGGCATTATGCCCAGTACATGACCTTATGGGACTTTCCTACT
hs5mie1   : ----------------------------A--------------------C-----G---* ad169hcmv : TGGCAGTACATCTACGTATTAGTCATCGCTATTACCATGGTGATGCGGTTTTGGCAGTAC
hs5mie1   : ------------------------------------------------------------ ad169hcmv : ATCAATGGGCGTGGATAGCGGTTTGACTCACGGGGATTTCCAAGTCTCCACCCCATTGAC
hs5mie1   : -C---------------------------------------------------------- ad169hcmv : GTCAATGGGAGTTTGTTTTGGCACCAAAATCAACGGGACTTTCCAAAATGTCGTAACAAC
hs5mie1   : --------------------------------------------------------T--- ad169hcmv : TCCGCCCCATTGACGCAAATGGGCGGTAGGCGTGTACGGTGGGAGGTCTATATAAGCAGA
hs5mie1   : C-------G--------------------------------------------------- ad169hcmv : GCTCGTTTAGTGAACCGTCAGATCGCCTGGAGACGCCATCCACGCTGTTTTGACCTCCAT
hs5mie1   : ------------------------------------------------------------ ad169hcmv : AGAAGACACCGGGACCGATCCAGCCTCCGCGGCCGGGAACGGTGCATTGGAACGCGGATT
hs5mie1   : ------------------------------------------------------------ ad169hcmv : CCCCGTGCCAAGAGTGACGTAAGTACCGCCTATAGAGTCTATAGGCCCACCCCCTTGGCT
hs5mie1   : --------------------------T----------------------...........

ad169hcmv : TCTTATGCATGCTATACTGTTTTTGGCTTG
hs5mie1   : ..............................
```

FIG. 6B(2)

```
LOCUS        HS5IEE       930 bp ds-DNA            VRL       15-SEP-1989
DEFINITION   Human cytomegalovirus major immediate-early gene, enhancer.
ACCESSION    K03104
KEYWORDS     major immediate-early gene.
SOURCE       HCMV strain AD169.
  ORGANISM   Human cytomegalovirus
             Viridae; ds-DNA enveloped viruses; Herpesviridae;
             Betaherpesvirinae.
REFERENCE    1  (bases 1 to 930)
  AUTHORS    Boshart,M., Weber,F., Jahn,G., Dorsch-Haesler,K.,
             Fleckenstein,B. and Schaffner,W.
  TITLE      A very strong enhancer is located upstream of an immediate
             early gene of human cytomegalovirus
  JOURNAL    Cell 41, 521-530 (1985)
  STANDARD   full automatic
REFERENCE    2  (sites)
  AUTHORS    Zhang,X.-Y., Inamdar,N.M., Supakar,P.C., Wu,K., Ehrlich,M.
             and Ehrlich,K.C.
  TITLE      three MDBP sites in the immediate-early enhancer-promoter
             region of human cytomegalovirus
  JOURNAL    Virology 182, 865-869 (1991)
  STANDARD   full automatic
COMMENT      Draft entry and printed copy of sequence in [1] were kindly
             provided by M.Boshart, 24-OCT-1985.
```

FIG. 6B(3)

```
FEATURES             Location/Qualifiers
     misc_signal     214..620
                     /note="HCMV IE enhancer region"
     mRNA            738..>930
                     /note="HCMV IE mRNA"

BASE COUNT      233 A     228 C     211 G     258 T
ORIGIN          12 bp upstream of BalI site; .750 mu.
  1 AATCAATATT GGCCATTAGC CATATTATTC ATTGGTTATA TAGCATAAAT CAATATTGGC
 61 TATTGGCCAT TGCATACGTT GTATCCATAT CATAAATATGT ACATTTATAT TGGCTCATGT
121 CCAACATTAC CGCCATGTTG ACATTGATTA TTGACTAGTT ATTAATAGTA ATCAATTACG
181 GGGTCATTAG TTCATAGCCC ATATATGGAG TTCCGCGTTA CATAACTTAC GGTAAATGGC
241 CCGCCTGGCT GACCGCCCAA CGACCCCCGC CCATTGACGT CAATAATGAC GTATGTTCCC
301 ATAGTAACGC CAATAGGGAC TTTCCATTGA CGTCAATGGG TGGAGTATTT ACGGTAAACT
361 GCCCACTTGG CAGTACATCA AGTGTATCAT ATGCCAAGTA CGCCCCCTAT TGACGTCAAT
421 GACGGTAAAT GGCCCGCCTG GCATTATGCC CAGTACATGA CCTTATGGGA CTTTCCTACT
481 TGGCAGTACA TCTACGTATT AGTCATCGCT ATTACCATGG TGATGCGGTT TTGGCAGTAC
541 ATCAATGGGC GTGGATAGCG GTTTGACTCA CGGGGATTTC CAAGTCTCCA CCCCATTGAC
601 GTCAATGGGA GTTTGTTTTG GCACCAAAAT CAACGGGACT TTCCAAAATG TCGTAACAAC
661 TCCGCCCCAT TGACGCAAAT GGGCGGTAGG CGTGTACGGT GGGAGGTCTA TATAAGCAGA
721 GCTCGTTTAG TGAACCGTCA GATCGCCTGG AGACGCCATC CACGCTGTTT TGACCTCCAT
781 AGAAGACACC GGGACCGATC CAGCCTCCGC GGCCGGGAAC GGTGCATTGG AACGCGGATT
841 CCCCGTGCCA AGAGTGACGT AAGTACCGCC TATAGAGTCT ATAGGCCCAC CCCCTTGGCT
901 TCTTATGCAT GCTATACTGT TTTTGGCTTG
                                                               (SEQ ID NO:2)
```

FIG. 6B(4)

| | |
|---|---|
| LOCUS | HS5MIE1 616 bp ds-DNA VRL 15-SEP-1989 |
| DEFINITION | Human cytomegalovirus (Towne) major immediate-early (IE) gene, exon 1. |
| ACCESSION | K01484 K01090 |
| KEYWORDS | major immediate-early gene. |
| SEGMENT | 1 of 4 |
| SOURCE | Human cytomegalovirus (strain Towne) passed in primary human foreskin fibroblasts, DNA [1], clone pXEP22 [2]. |
| ORGANISM | Human cytomegalovirus<br>Viridae; ds-DNA enveloped viruses; Herpesviridae; Betaherpesvirinae. |
| REFERENCE | 1 (bases 460 to 616) |
| AUTHORS | Stenberg,R.M., Thomsen,D.R. and Stinski,M.F. |
| TITLE | Structural analysis of the major immediate early gene of human cytomegalovirus |
| JOURNAL | J. Virol. 49, 190-199 (1984) |
| STANDARD | full automatic |
| REFERENCE | 2 (bases 1 to 490) |
| AUTHORS | Thomsen,D.R., Stenberg,R.M., Goins,W.F. and Stinski,M.F. |
| TITLE | Promoter-regulatory region of the major immediate early gene of human cytomegalovirus |
| JOURNAL | Proc. Natl. Acad. Sci. U.S.A. 81, 659-663 (1984) |
| STANDARD | full automatic |
| COMMENT | IE region 1 gene is also known as the major IE gene. |

FIG. 6B(5)

```
FEATURES             Location/Qualifiers
     prim_transcript 490..>616
                     /note="major IE mRNA"
     intron          611..>616
                     /note="major IE mRNA intron A"

BASE COUNT     144 A    165 C    162 G    145 T
ORIGIN      28 bp upstream of HincII site; 0.752 map units.
  1 GGCGACCGCC CAGCGACCCC CGCCCGTTGA CGTCAATAGT CGTCAATAGT GACGTATGTT CCCATAGTAA
 61 CGCCAATAGG GACTTTCCAT TGACGTCAAT GGGTGGAGTA GGGCGCCCCC TATTGACGTC AATGACGGTA
121 TGGCAGTACA TCAAGTGTAT CATATGCCAA GTCCGCCCCC TATTGACGTC AATGACGGTA
181 AATGGCCCGC CTAGCATTAT GCCCAGTACA TGACCTTACG GGAGTTTCCT ACTTGGCAGT
241 ACATCTACGT ATTAGTCATC GCTATTACCA TGGTGATGCG GTTTTGGCAG TACACCAATG
301 GGCGTGGATA GCGGTTTGAC TCACGGGGAT TTCCAAGTCT CCACCCCATT GACGTCAATG
361 GGAGTTTGTT TTGGCACCAA AATCAACGGG ACTTTCCAAA ATGTCGTAAT AACCCCGCCC
421 CGTTGACGCA AATGGGCGGT AGGCGTGTAC GGTGGGAGGT CTATATAGCA GAGCTCGTTT
481 AGTGAACCGT CAGATCGCCT GGAGACGCCA TCCACGCTGT TTTGACCTCC ATAGAAGACA
541 CCGGACCGA TCCAGCCTCC GCGGCCGGGA ACGGTGCATT GGAACGCGGA TTCCCCGTGC
601 CAAGAGTGAC GTAAGT
```

(SEQ ID NO:3)

FIG. 6B(6)

HCMV (AD169) -> Full Restriction Map

DNA sequence    930 b.p.    aatcaatattgg ... gtttttggcttg    linear    (SEQ ID NO:4)

Positions of Restriction Endonucleases sites (unique sites underlined)

```
      Hae III                                              Hae III
      Msc I                                                Msc I
      Hae I                                                Hae I
Ssp I Eae I                                         Ssp I  Eae I         Mae II
  |     |                                             |     |              |
AATCAATATTGGGCCATTAGCCATTAGCCATTAGCCATATATTATTCATTGGTTATATATAGCATAAATCAATATTGGCTATTCAATATTGGCCATTGCATACGTT  80
TTAGTTATAACCCGGTAATCGGTAATCGGTAATCGGTATATAATAAGTAACCAATATATCGTATTTAGTTATAATCGATAAGTTATAAGCCGGTAACGTATGCAA
  |     |                                             |     |    |              |
  1     5                                             52    64   64             76
                                                            64
                                                            65

Mme I                        HinC II                  Mae I
      Rsa I Nla III                Nla III                        Spe I
        |     |                      |     |                        ||
GTATCCATATCATAATAATATGTACATTTATATTGGCTCATGTCCAACATTACCGCCATGTTGACATTGATTATTGACTAGTT  160
CATAGGTATAGTAGTTATTATACATGTAAATATAACCGAGTACAGGTTGTAATGGCGGTACAACTGTAACTAATAACTGATCAA
        |     |                      |     |                        ||
        99   116                    134   137                      154
             120                                                   155
```

FIG. 6C(1)

```
Mse I                                                    Bgl I
Age I                                       Mae III      Sau96 I
 | |                                        BstU I       Hae III
 | |                                          | |         | | |
ATTAATAGTAATCAATTACGGGGTCATTAGTTCATATAGCCCATATATGGAGTTCCGCGTTACATAACTTACGGTAAATGGC
TAATTATCATTAGTTAATGCCCCAGTAATCAAGTATATCGGGTATATACCTCAAGGCGCAATGTATTGAATGCCATTTACCG  240
 | |                                          | |         | | |
161                                          214        238
161                                          217        238
162                                                     239

ScrF I                Mae II                                        Mae III
EcoR II               Aha II                       Mae II              |
BstN I                Aat II                         |                 |
  |                     | |                          |                 |
CCGCCTGGCTGACCGCCCAACGACCCCCGCCCATTGACGTCAATAATGACGTATGTTCCCATAGTAACGCCAATAGGGAC
GGCCGGACCGACTGGCGGGTTGCTGGGGGCGGGTAACTGCAGTTATTACTGCATACAAGGGTATCATTGCGGTTATCCCTG  320
  |                     | |                          |                 |
244                   276                          289                304
244                   276
244                   277

Bgl I    Rsa I                 Nde I      Rsa I
 Mae II                                      |        |                     |          |
 Aha II                                      |        |                     |          |
 Aat II                                      |        |                     |          |
   | |                                       |        |                     |          |
TTTCCATTGACGTCAATGGGTGGAGTATTTACGGTAAACTGCCCACTTGGCAGTACATCAAGTGTATCATATGCCAAGTA
AAAGGTAACTGCAGTTACCCACCTCATAAATGCCATTTGACGGGTGAACCGTCATGTAGTTCACATAGTATACGGTTCAT  400
   | |                                       |        |                     |          |
329                                        361      373                   388        398
329
330

FIG. 6C(2)
```

```
                                                                    Nla III
                    ScrF I
                    EcoR II
                    BstN I
        Mae II      Bgl I
        Aha II      Sau96 I                         Rsa I
        Aat II      Hae III                         Bsr I
         ||           ||                              ||                                    |
CGCCCCCTATTGACGTCAATGACGGTAAATGGCCCGCCTGGCATTATGCCCAGTACATGACCTTATGGGACTTTCCTACT      480
GCGGGGGATAACTGCAGTTACTGCCATTTACCGGGCGGACCGTAATACGGGTCATGTACTGGAATACCCTGAAAGGATGA
         ||           ||                              ||    ||   |
        412          431                             450   453
        412          431                                    456
        413          432
                                        Hph I
                                        Nla III
                                        Sty I
                                        Sec I                          Rsa I
        Mae II                          Nco I             SfaN I
        SnaB I                          Dsa I               |            |
Rsa I   BsaA I                           ||                 ||           |                  |
  |       ||                            ||                 ||           |
TGGCCAGTACATCTACGTATTAGTCATCGCTATTACCATGGTGCAGTACATCAATGGGCGTGGATAGCG              560
ACCGGTCATGTAGATGCATAATCAGTAGCGATAATGGTACCACACGTCATGTAGTTACCCGCACCTATCGC
  |       ||                            ||                 ||           |
 486     493                            515                516          519          522          537
         493                            515
         494                            515
                                        515

FIG. 6c(3)
```

EXPRESSION OF CLONED GENES IN THE LUNG BY AEROSOL AND LIPOSOME-BASED DELIVERY

CROSS-REFERENCE TO RELATED APPLICATIONS

This application is a continuation of and claims the benefit of U.S. application Ser. No. 07/972,135, filed Nov. 5, 1992, now U.S. Pat. No. 5,858,784, which is a continuation-in-part of Ser. No. 07/809,291, filed Dec. 17, 1991 now abandoned, the disclosure of which is incorporated by reference.

INTRODUCTION

1. Technical Field

The present invention relates to methods and compositions for producing a transgenic mammal which expresses an exogenously supplied gene in lung tissue. The gene is supplied by aerosolized delivery, particularly to the airways and alveoli of the lung.

2. Background

With the advent of molecular cloning techniques, an expanding array of genes with mutations responsible for important human diseases have been identified and isolated. To date, attempts to replace absent or mutated genes in human patients have relied on ex vivo techniques. Ex vivo techniques include transformation of cells in vitro with either naked DNA or DNA encapsulated in liposomes, followed by introduction into a host organ ("ex vivo" gene therapy). The criteria for a suitable organ include that the target organ for implantation is the site of the relevant disease, the disease is easily accessible, that it can be manipulated in vitro, that it is susceptible to genetic modification methods and ideally, it should contain either non-replicating cells or cycling stem cells to perpetuate a genetic correction. It also should be possible to reimplant the genetically modified cells into the organism in a functional and stable form. A farther requirement for ex vivo gene therapy, if for example a retroviral vector is used, is that the cells be pre-mitotic; post-mitotic cells are refractory to infection with retroviral vectors. Exemplary of a target organ which meets the criteria of in vitro gene transfer is the mammalian bone marrow.

There are several drawbacks to ex vivo therapy. For example, if only differentiated, replicating cells are infected, the newly introduced gene function will be lost as those cells mature and die. Ex vivo approaches also can be used to transfect only a limited number of cells and cannot be used to transfect cells which are not first removed from the body.

Retroviruses, adenoviruses and liposomes have been used in animal model studies in attempts to increase the efficiency of gene transfer; DNA has been introduced into animals by intratracheal (IT), intravenous, intraperitoneal, intramuscular, and intraarterial injection. Expression of introduced genes, either complexed to cationic liposomes or packaged in adenoviral vectors has been demonstrated in the lungs of rodents after IT instillation. However, IT injection is invasive and produces a non-uniform distribution of the instilled material; it also is too invasive to be performed repeatedly in humans. It therefore would be of interest to develop a non-invasive delivery technique which also results in deeper penetration of material into the lung than other methods, and can be used to deposit material evenly throughout the airways and alveoli. Such a delivery technique could be used as a means of treatment for genetic disorders, particularly of the lung, via generalized transgene expression in lung cells in vivo.

Relevant Literature

Hazinski, et al., *Am. J. Respir. Cell Mol. Biol.* (1991) 4:206–209, relates to liposome-mediated gene transfer of DNA into the intact rodent lung. Three fusion gene constructs were complexed to cationic liposomes including (1) the chloramphenicol acetyltransferase ("CAT") gene linked to a Rous sarcoma virus ("RSV") promoter; (2) the CAT gene linked to a mouse mammary tumor virus ("MMTV") promoter; and (3) a cytomegalovirus-$\beta$-galactosidase ("CMV-$\beta$-gal") fusion gene. The liposome/DNA complexes were instilled into the cervical trachea of rats and detectable levels of gene expression observed. Brigham et al, *Am. J. Med. Sci.* (1989) 298:278–281, describes the in vivo transfection of murine lungs with the CAT gene using a liposome vehicle. Transfection was accomplished by intravenous, intratracheal or intraperitoneal injection. Both intravenous and intratracheal administration resulted in the expression of the CAT gene in the lungs. However, intraperitoneal administration did not. Canonico et al., *Clin. Res.* (1991) 39:219A describes the expression of the human $\alpha$-1 antitrypsin gene, driven by the CMV promoter, in cultured bovine lung epithelial cells. The gene was added to cells in culture using cationic liposomes. The experimenters also detected the presence of $\alpha$-1 antitrypsin in histological sections of the lung of New Zealand white rabbits following the intravenous delivery of gene constructs complexed to liposomes. Wolff et al., *Science* (1990) 247:1465–1468 relates to direct transfer of the CAT, $\beta$-gal and luciferase genes into mouse skeletal muscle in vivo. Gene expression was observed in all three cases. Nabel et al., *Science* (1990) 249:1285–1288, pertains to in vivo intra-arterial transfection of pigs with liposomes containing a $\beta$-gal expression plasmid. Site-specific gene expression was observed in the arterial wall. None of the above cited art, however, practices or teaches the use of aerosol administration to deliver genes directly to the lung.

PCT/US90/01515, having International Publication No. WO 90/11092, describes a method for introducing naked DNA into muscle tissue. Yoshimura et al. disclose expression of the human cystic fibrosis transmembrane conductance regulator gene in mouse lung after intratracheal plasmid-mediated gene transfer. Debs et al. disclose pentamidine uptake in the lung by aerosolization and delivery in liposomes. *Am Rev Respir Dis* (1987) 135: 731–737.

SUMMARY

Methods and compositions are provided for producing a mammal which expresses an exogenously supplied gene of interest in cells of the lung. The method includes the steps of preparing a liposome-nucleic acid mixture suitable for nebulization, nebulizing the mixture, and depositing the resulting nebulized mixture in the lung of a mammalian host of interest in an amount sufficient to transform cells contacted by the deposited nebulized mixture. The exogenously supplied gene generally is provided in an expression cassette and includes a coding sequence operably joined to transcriptional and translational regulatory sequences functional in the mammalian host. The methods and compositions find use as in vivo gene therapy of pulmonary disorders.

BRIEF DESCRIPTION OF THE FIGURES

FIG. 1 demonstrates that aerosol administration of pRSV-CAT-DOTMA: cholesterol complexes resulted in expression of the CAT gene in mouse lungs. Lanes 1–3 were derived from mice receiving no treatment; lanes 4–6 represent mice administered 0.5 mg pRSV-CAT with 1.0 μmole DOTMA-cholesterol liposomes; lanes 7–9 were derived from mice receiving 2.0 mg pRSV-CAT alone; and lanes 10–12 represent mice given 2.0 mg pRSV-CAT with 4.0 μmol DOTMA-cholesterol liposomes in a 2 to 1 molar ratio. The CAT gene is not normally present in mammalian cells; the results thus indicate that the lung was successfully transfected by the pRSV-CAT DOTMA-cholesterol:liposome aerosol. The results also show that neither aerosol administration of the pRSV-CAT alone, nor a lower aerosol dose of pRSV-CAT: DOTMA-cholesterol complexes produce detectable expression of the CAT gene in mouse lungs. Thus, both the cationic liposome carrier, and a sufficient dose of DOTMA: liposome complexes are required to produce transgene expression in the lung after aerosol administration.

FIG. 2 shows the results of an experiment where mice were administered 12 mg of pCIS-CAT complexed to 24 μmoles of DOTMA/DOPE 1:1 liposomes. Lanes 1-3 show the results from animals administered the aerosol in an Intox-designed nose-only aerosol exposure chamber; lanes 4–7 are derived from mice exposed to the aerosol in a modified mouse cage; and lanes 8–10 show the results from animals placed in a smaller modified cage after being put in restrainers originally constructed for use in the Intox chamber.

Figure 6A:
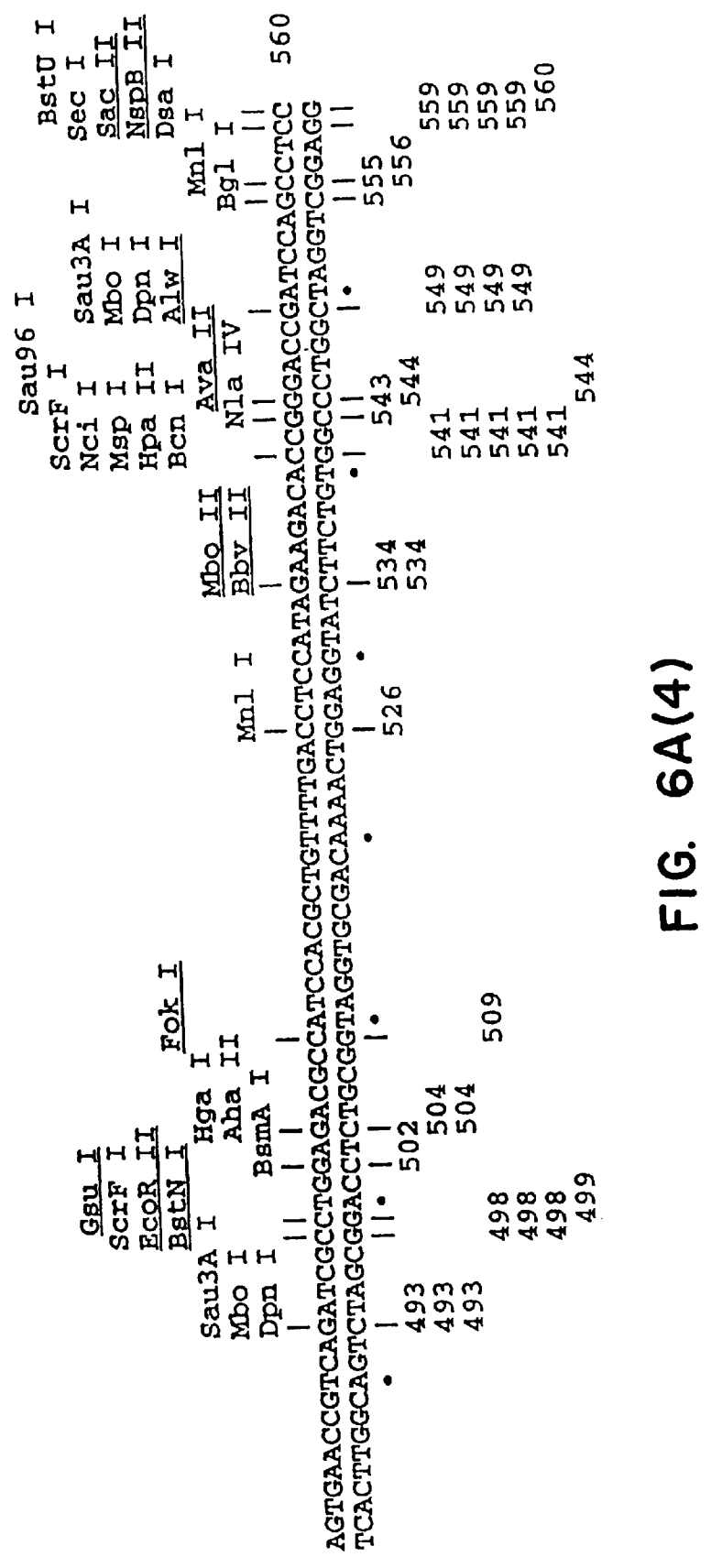
Figure 1:
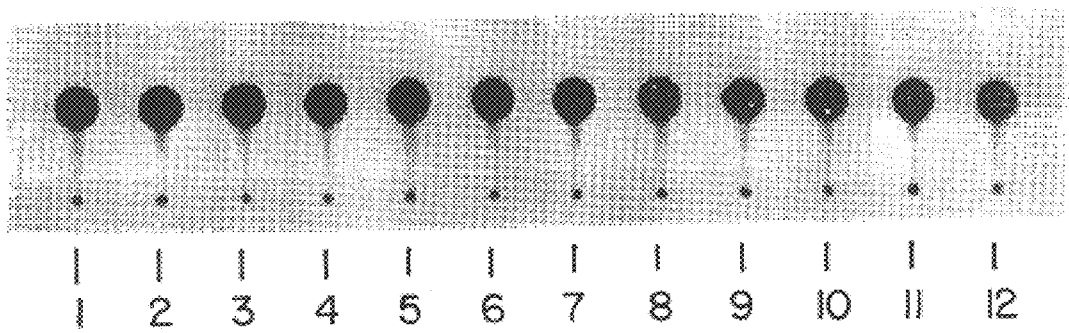

FIG. 6 shows a full restriction map for HCMV (Towne) of the immediate early enhancer and promoter region of HCMV (Towne) (SEQ ID NO:1) in FIG. 6A and HCMV (AD169) (SEQ ID NO:4) in FIG. 6C. FIG. 6B shows a sequence comparison of the 2 HCMV promoters, ad169hcmv (SEQ ID NO:2) and hs5miel (SEQ ID NO:3). The sequence of the Towne strain is designated as hs5miel on this comparison. The position of the NcoI site is indicated by an asterik.

DESCRIPTION OF THE SPECIFIC EMBODIMENTS

In accordance with the subject invention, nucleic acid constructs together with methods of preparation and use are provided which allow for in vivo modulation of phenotype of cells in the respiratory tract of a mammalian host following delivery of a sufficient dose of a liposome-nucleic acid aerosol to the host mammal. The liposome-nucleic acid aerosol is obtained by nebulization of a liposome-nucleic acid samplex mixture prepared in a biologically compatible fluid that minimizes aggregation of the liposome-nucleic complexes. The methods and compositions can be used to produce a mammal capable of expressing an exogenously supplied gene in lung tissue, particularly alveolar and airway passage cells.

Central to the present invention is the discovery that genes can be delivered to the lung via aerosol administration, and subsequently expressed in vivo. The instant invention takes advantage of the use of liposomes as a delivery mechanism. Liposomes are able to stably bind through charge interactions or entrap and retain nucleic acid and permit a system amenable to nebulization, whereby intact genes can be delivered to specific pulmonary tissues. Particular sites in the lung are targeted by varying the size of the aerosol particles administered, as discussed more fully below. Targeting agents, such as antibodies directed against surface antigens expressed on specific pulmonary cell types, can also be covalently conjugated to the liposomal surface so that nucleic acid can be delivered to specific cell types.

Liposomes also allow for the delivery of relatively large amounts of nucleic acid, without a toxic effect, such that therapeutically effective amounts of the desired protein can be expressed in vivo. For a review of the use of liposomes as carriers for delivery of nucleic acids, see, Hug and Sleight, *Biochim. Biophys. Acta.* (1991) 1097:1–17; Straubinger et al., in *Methods of Enzymology* (1983), Vol. 101, pp. 512–527.

Liposomes have been used effectively, particularly to introduce drugs, radiotherapeutic agents, enzymes, viruses, transcription factors and other cellular effectors into a variety of cultured cell lines and animals. In addition, successful clinical trials examining the effectiveness of liposome-mediated delivery of small drug molecules and peptides which act extracellularly have been reported. Several strategies have been devised to increase the effectiveness of liposome-mediated drug delivery by targeting liposomes to specific tissues and specific cell types. However, while the basic methodology for using liposome-mediated vectors is well developed and has been shown to be safe, the technique previously has not been perfected for liposome-based transfection vectors, and particularly not for aerosolized delivery to pulmonary tissue for in vivo gene therapy. By in vivo gene therapy is meant expression of introduced nucleic acid sequences to prevent, palliate and/or cure animal or human disease.

In addition to discovering that transformation of lung cells can be obtained using aerosolized liposome nucleic acid constructs, Applicants have identified several factors that can affect the relative ability of particular liposome-nucleic acid constructs to provide transformation of lung cells following aerosolized delivery of a solution containing the liposome-nucleic acid constructs and to achieve a high level of expression. These factors include preparation of a solution that prior to or during nebulization will not form macroaggregates and wherein the nucleic acid is not sheared into fragments and preparation both of liposomes and of expression constructs, that provide for predictable transformation of host lung cells following aerosolization of the liposome-nucleic acid complex and administration to the host animal. These factors are discussed in detail below.

Aerosol delivery of nucleic acid-liposome complexes provides a number of advantages over other modes of administration. For example, aerosol administration can serve to reduce host toxicity. Such an effect has been observed with the delivery of substances such as pentamidine and cytokines, which can be highly toxic when delivered systematically, but are well tolerated when aerosolized. See, e.g., Debs et al., *Antimicrob. Agents Chemother.* (1987) 31:37–41; Debs et al, *Amer. Rev. Respir. Dis.* (1987) 135:731–737; Debs et al., *J. Immunol.* (1988) 140:3482–3488; Montgomery et al., *Lancet* (1987) 11:480–483; Montgomery et al., *Chest* (1989) 95:747–751; Leoung et al., *N. Eng. J. Med.* (1990) 323:769–775. Additionally, rapid clearance of circulating liposomes by the liver and spleen reticuloendothelial system is avoided, thereby allowing the sustained presence of the administered substance at the site of interest, the lung. Serum induced inactivation of the therapeutic agent is also reduced.

Other advantages of the subject invention include ease of administration i.e., the host mammal simply inhales the aerosolized liposome-nucleic acid solution into the intended tissue, the lung. Further, by varying the size of the nebulized particles some control may also be exercised over where in the lung the aerosol is delivered. Delivery may be extended over a long time period. Thus, there is a significant increase in the time period that target cells are exposed to the expression constructs. Distribution of the aerosol is even throughout areas of the lung accessible to the spray. These advantages are significant, particularly when compared to other routes of administration such as intratracheal delivery which is invasive, the expression constructs are delivered in a bolus which may disrupt the mucous barrier and additionally may result in pooling of the introduced fluid in areas of the lung at lower elevation. Further, damage from insertion of the intratracheal tube may alter the ability of cells coming into contact with the expression constructs to be transfected.

The type of vector used in the subject application may also be an advantage. For example, most gene therapy strategies have relied on transgene insertion into retroviral or DNA virus vectors. Potential disadvantages of retrovirus vectors, as compared to the use of liposomes, include the limited ability of retroviruses to mediate in vivo (as opposed to ex vivo) transgene expression; the inability of retrovirus vectors to transfect non-dividing cells; possible recombination events in replication-defect of retrovirus vectors, resulting an infectious retroviruses; possible activation of oncogenes or inhibition of tumor suppressor genes due to the random insertion of the transgene into host cell genomic DNA; size limitations (less than 15 kb of DNA that can be packaged); and potential aminogenosity leading to a host immune response against the vector. In addition, all ex vivo approaches require that the cells removed from the body be maintained in culture for a period of time. While in culture, cells may undergo deleterious or potentially dangerous phenotypic and/or genotypic changes. Adenovirus and other DNA viral vectors share several of the above potential limitations.

The nucleic acid constructs generally will be provided as expression cassettes which will include as operably linked components in the direction of transcription, a transcriptional initiation region, a nucleic acid sequence of interest and a transcriptional termination region wherein the transcriptional regulatory regions are functional in the mammalian host lung cell. An intron optionally may be included in the construct, preferably $\geq 100$ bp and placed 5' to the coding sequence. Desirably, the construct does not become integrated into the host cell genome and is introduced into the host as part of a non-integrating expression vector. A coding sequence is "operably linked to" or "under the control of" control sequences in a cell when DNA polymerase will bind the promoter sequence and transcribe the coding sequence into mRNA, which is then translated into the polypeptide encoded by the coding sequence. The nucleic acid sequence includes DNA sequences which encode polypeptides which are directly or indirectly responsible for a therapeutic effect, as well as genes coding for active nucleotide sequences such as antisense sequences and ribozymes.

In some cases, it may be desirable to use constructs that produce a long term transgene expression in vivo, either by integration into host cell genomic DNA at high levels or by persistence of the transgene in the nucleus of cells in vivo in stable, episomal form. Integration of the transgene into genomic DNA of host cells in vivo may be facilitated by administering the transgene in a linearized form (either the coding region alone, or the coding region together with 5' and 3' regulatory sequences, but without any plasmid sequences present). It may be possible to further increase the incidence of transgene integration into a genomic DNA by incorporating a purified retroviral enzyme, such as the HIV-1 integrase enzyme, into the liposome-DNA complex. Appropriate flanking sequences are placed at the 5' and 3' ends of the transgene DNA. These flanking sequences have been shown to mediate integration of the HIV-1 DNA into host cell genomic DNA in the presence of HIV-1 integrase. Alternatively, the duration of the transgene expression in vivo can be prolonged by the use of constructs that contain non-transforming sequences of a virus such as Epstein-Barr virus, sequences such as oriP and EBNA-1 which appear to be sufficient to allow heterologous DNA to be replicated as an episome in mammalian cells (Buhans et al., *Cell* (1986) 52:955).

Isolation of Genes and Construction of Vectors

Nucleic acid sequences, for use in the present invention, can be derived from known sources, for example by isolating the nucleic acid from cells containing the desired gene, using standard techniques. Similarly, the gene sequence can be generated synthetically, using standard modes of polynucleotide synthesis, well known in the art. See, e.g. Edge, M. D., *Nature* (1981) 292:756; Nambair, et al., *Science* (1984) 223:1299; Jay, Ernest, *J. Biol Chem* (1984) 259:63 11. Generally, synthetic oligonucleotides are prepared by either the phosphotriester method as described by Edge et al., *Nature* (supra) and Duckworth et al., *Nucleic Acids Res* (1981) 9:1691, or the phosphoramidite method as described by Beaucage, S. L., and Caruthers, M. H., *Tet. Letts.* (1981) 22:1859, and Matteucci, M. D., and Caruthers, M. H., *J. Am. Chem. Soc.* (1981) 103:3185, and can be prepared using commercially available automated oligonucleotide synthesizers. The gene sequence can be designed with the appropriate codons for the particular amino acid sequence. In general, one will select preferred codons for expression in the intended host. The complete sequence is assembled from overlapping oligonucleotides prepared by standard methods and assembled into a complete coding sequence. See, e.g., Edge (1981) *Nature* 292:756; Nambair et al., (1984) *Science* 223:1299; Jay et al., (1984) *J. Biol. Chem.* 259:6311.

A particularly convenient method for obtaining nucleic acid for use in the liposome-nucleic acid preparations, is by recombinant means. Thus, the desired gene can be excised from a plasmid carrying the desired gene, using standard restriction enzymes and procedures. Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. If desired, size separation of the cleaved fragments may be performed by polyacrylamide gel or agarose gel electrophoresis using standard techniques. A general description of size separations is found in *Methods in Enzymology* (1950) 65:499–560.

Restriction cleaved fragments may be blunt ended by treating with the large fragment of *E. coli* DNA polymerase I (Klenow) in the presence of the four deoxynucleotide triphosphates (dNTPs) using standard techniques. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture can be extracted with e.g. phenol/chloroform, and ethanol precipitated. Treatment under appropriate conditions with S1 nuclease or BAL-31 results in hydrolysis of any single-stranded portion.

Once coding sequences for the desired proteins have been prepared or isolated, they can be cloned into any suitable vector or replicon. Numerous cloning vectors are known to those of skill in the art; the selection of an appropriate cloning vector is known to those of skill in the art, and the selection of an appropriate cloning vector is a matter of choice. Ligation to other sequences is performed using standard procedures, known in the art. For example, ligations can be accomplished in 20 mM Tris-Cl pH 7.5, 10 mM $MgCl_2$, 10 mM DTT, 33 ug/ml BSA, 10 mM-50 mM NaCl, and either 40 uM ATP, 0.01–0.02 (Weiss) units T4 DNA ligase at 0° C. (for "sticky end" ligation) or 1 MM ATP, 0.3–0.6 (weiss) units T4 DNA ligase at 14° C. (for "blunt end" ligation). Intermolecular "sticky end" ligations are usually performed at 30–100 ug/ml total DNA concentration (5–100 nM total end concentration).

The coding sequence for a polypeptide of interest can be placed under the control of a promoter, ribosome binding site and, optionally, an operator (collectively referred to herein as "control" elements), so that the gene sequence encoding the desired protein is transcribed into RNA in the host tissue transformed by a vector containing this expression construct. The coding sequence may or may not contain a signal peptide or leader sequence. A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the transcription start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Nucleic acid "control sequences" or "regulatory elements" refer collectively to promoter sequences, ribosome binding sites, polyadenylation signals, transcription termination sequences, upstream regulatory domains, enhancers, and the like, which collectively provide for the transcription and translation of a coding sequence in a host cell.

The choice of regulatory elements will depend on the host cell which is to be transformed and the type of liposomal preparation used. Thus, if the host cells' endogenous transcription and translation machinery will be used to express the polypeptide of interest, control elements functional in the particular host will be used. Several promoters for use in mammalian cells are known in the art and include, but are not limited to, SV40 (Simian Virus 40) early promoter, the RSV (Rous Sarcoma Virus) promoter, the Adenovirus major late promoter, and the human CMV (Cytomegalovirus) immediate early one promoter. Other promoters which may be used include those derived from mouse mammary tumor virus (MMTV, T7, T3, and the like). Particularly useful in the present invention is the RSV promoter, and the CMV promoter, particularly the AD169 strain of CMV.

In addition to control sequences, it may be desirable to add regulatory sequences which allow for regulation of the expression of the polypeptide of interest sequences. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences. Such regulatory elements include the P-interferon, heat shock, metallothionein or steroid hormone responsive genes, including insect genes such as the ecdysone receptor gene. Such promoters can be used to regulate expression of the transgene by the use of external stimuli such as interferon or glucocorticoids. Since the arrangement of eukaryotic promoter elements is highly flexible, combinations of constitutive and inducible elements can be used. Tandem arrays of two or more inducible promoter elements may increase the level of induction above baseline levels of transcription which can be achieved with a single inducible element. By transcription enhancer elements are intended DNA sequences which are primary regulators of transcriptional activity which can act to increase transcription from a promoter element, and generally do not have to be in the 5' orientation with respect to the promoter in order to enhance transcriptional activity.

The combination of promoter and enhancer elements used in a particular expression cassette can be selected by one skilled in the art to maximize specific effects. Different enhancer elements can be used to produce a desired level of transgene expression. For example, a tissue specific promoter such as that derived from the human cystic fibrosis transmembrane conductance regulator (CFTR) gene can be used flanking a very active, heterologous enhancer element, such as the SV40 enhancer, in order to obtain both a high level of expression and expression of the transgene in lung. Tandem repeats of two or more enhancer elements or combinations of enhancer elements may significantly increase transgene expression when compared to the use of a single copy of an enhancer element. The use of two different enhancer elements from the same or different sources, flanking or within a single promoter may be used. Evaluation of particular combinations of enhancer elements for a particular desired effect or expression level is within the knowledge of one skilled in the art. Promoter-enhancer elements are least partially derived from CMV Townes and/or AD169 strains are of particular interest for providing a high level of expression of a polypeptide of interest.

The termination region which is employed primarily will be one of convenience, since termination regions appear to be relatively interchangeable. The termination region may be native to the intended nucleic acid sequence of interest, or may be derived from another source. Convenient termination regions are available and include the 3' end of a gene terminator and polyadenylation signal from the same gene from which the 5' regulatory region is obtained. Adenylation residues, preferably more than 32 and up to 200 or more if necessary may be included in order to stabilize the mRNA. Alternatively, a terminator and polydenylation signal from different gene/genes may be employed with similar results. Specific sequences which regulate post-transcriptional mRNA stability may optionally be included. For example, certain polyA sequences (Volloch et al., *Cell* (1981) 23:509) and β-globin MRNA elements can increase mRNA stability, whereas certain AU-rich sequences in MRNA can decrease MRNA stability (Shyu et al., *Genes and Development* (1989) 3:60). In addition, AU regions in 3' non-coding regions may be used to destabilize MRNA if a short half life mRNA is desirable. A 3'-intron should be avoided, particularly a SV40 3'-intron.

The construct may include sequences for selection, such as a neomycin resistance gene, dihydrofolate reductase gene, and/or signal sequences to regenerate recombinant proteins that are targeted to different cellular compartment or secreted when the wild type sequence is not. Any of a variety of signal sequences may be used which are well known to those skilled in the art. The signal sequences may allow generation of new vaccine strategies or produce soluble antagonists directly against specific cell surface receptors such as transformed oncogenes. The sequences for selection may be on a separate plasmid and cotransfected with the plasmid carrying the nucleic acid coding for the therapeutic polypeptide. The selection plasmid may be complexed to a different carrier or to the same carrier as the therapeutic plasmid.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

It may be desirable to produce mutants or analogs of the proteins of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., infra; DNA Cloning, Vols. I and II, supra; Nucleic Acid Hybridization, infra.

If the gene sequence of the desired protein is not known, it can be obtained using the following general techniques. The desired protein can be isolated from, for example, tissue samples containing the same. This is generally accomplished by first preparing a crude extract which lacks tissue components and several extraneous proteins. The desired proteins can then be further purified i.e. by column chromatography, HPLC, immunoabsorbent techniques or other conventional methods well known in the art. Purification of the protein permits the sequencing of the same by any of the various methods known to those skilled in the art. For example, the amino acid sequences of the subject proteins can be determined from the purified proteins by repetitive cycles of Edman degradation, followed by amino acid analysis by HPLC. Other methods of amino acid sequencing are also known in the art.

Once the amino acid sequences are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. I, supra; *Nucleic Acid Hybridization*, supra; *Oligonucleotide Synthesis*, supra; Sambrook, et al., supra. First, a DNA library is prepared. The library can consist of a genomic DNA library from the species of choice. Once the library is constructed, oligonucleotides to probe the library are prepared and used to isolate the gene encoding the desired protein. The oligonucleotides are synthesized by any appropriate method. The particular nucleotide sequences selected are chosen so as to correspond to the codons encoding a known amino acid sequence from the desired protein. Since the genetic code is degenerate, it will often be necessary to synthesize several oligonucleotides to cover all, or a reasonable number, of the possible nucleotide sequences which encode a particular region of the protein. Thus, it is generally preferred in selecting a region upon which to base the probes, that the region not contain amino acids whose codons are highly degenerate.

In certain circumstances, one of skill in the art may find it desirable to prepare probes that are fairly long, and/or encompass regions of the amino acid sequence which would have a high degree of redundancy in corresponding nucleic acid sequences, particularly if this lengthy and/or redundant region is highly characteristic of the protein of interest. It may also be desirable to use two probes (or sets of probes), each to different regions of the gene, in a single hybridization experiment. Automated oligonucleotide synthesis has made the preparation of large families of probes relatively straight-forward. While the exact length of the probe employed is not critical, generally it is recognized in the art that probes from about 14 to about 20 base pairs are usually effective. Longer probes of about 25 to about 60 base pairs are also used.

The selected oligonucleotide probes are labeled with a marker, such as a radionucleotide or biotin using standard procedures. The labeled set of probes is then used in the screening step, which consist of allowing the single-stranded probe to hybridize to isolated ssDNA from the library, according to standard techniques. Either stringent or permissive hybridization conditions could be appropriate, depending upon several factors, such as the length of the probe and whether the probe is derived from the same species as the library, or an evolutionary close or distant species. The selection of the appropriate conditions is within the skill of the art. See, generally, *Nucleic Acid hybridization,* supra. The basic requirement is that hybridization conditions be of sufficient stringency so that selective hybridization occurs; i.e., hybridization is due to a sufficient degree of nucleic acid homology (e.g., at least about 75%), as opposed to nonspecific binding. Once a clone from the screened library has been identified by positive hybridization, it can be confirmed by restriction enzyme analysis and DNA sequencing that the particular library insert contains a gene for the desired protein. The desired DNA sequence can then be cloned into a cloning vector and further used, as described below.

Preparation of Liposomes

Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid, resulting in a liposome-nucleic acid complex which will withstand both the forces of nebulization and the environment within the lung airways and be capable of transfecting lung cells after the aerosolized DNA:liposome complex has been deposited in the lung. Cationic liposomes have been shown to mediate intracellular delivery of plasmid DNA (Felgner, et al., *Proc. Natl. Acad. Sci. USA* (1987) 84:7413–7416); mRNA (Malone, et al., *Proc. Natl. Acad. Sci. USA* (1989) 86:6077–6081); and purified transcription factors (Debs, et al., *J. Biol. Chem.* (1990) 265:10189–10192), in functional form.

Liposomes can be prepared from a variety of cationic lipids, including DOTAP, DOTMA, DDAB, L-PE, and the like. Liposomes containing a cationic lipid, such as {N(1-2-3-dioleyloxy) propyl}-N,N,N-triethylammonium} (DOTMA), dimethyl dioctadecyl ammonium bromide (DDAB), or 1, 2-dioleoyloxy-3-(trimethylammonio) propane (DOTAP) or lysinylphosphatidylethanolamine (L-PE) and a second lipid, such as distearoylphosphatidylethanolamine (DOPE) or cholesterol (Chol), are of particular interest. DOTMA synthesis is described in Felgner, et al., *Proc. Nat. Acad. Sciences,* (USA) (1987) 84:7413–7417. DOTAP synthesis is described in Stamatatos, et al., *Biochemistry* (1988) 27:3917. DOTMA:DOPE liposomes can be purchased from, for example, BRL. DOTAP:DOPE liposomes can be purchased from Boehringer Mannheim. Cholesterol and DDAB are commercially available from Sigma Corporation. DOPE is commercially available from Avanti Polar Lipids. DDAB:DOPE can be purchased from Promega.

Cationic liposome:DNA complexes are internalized by cells by a classical receptor-mediated endocytosis using cell surface receptors which contain specific binding sites for, and are able to internalize, cationic molecules. Using agents such as cytokines, growth factors, other soluble proteins and certain drugs, it is thus possible to selectively up or down regulate these cation-binding receptors. The rate of up or down regulation of these receptors by the appropriate agent will allow selection of specific cells for enhanced or reduced levels of transfection in vivo. Thus, the use of specific cationic lipids can confer specific advantages for in vivo delivery. For example, iv injection of DOTAP-containing liposomes can target transgene expression primarily to the lung and may offer increased advantages for aerosolized delivery. Furthermore, DOTAP, as well as L-PE and CEBA are fully metabolized by cells, whereas DOTMA cannot be fully metabolized by cells. Therefore, DOTAP and L-PE, but not DOTMA, are suitable for repeated administration to mammalian hosts. Additionally, complexing the cationic lipid with a second lipid, primarily either cholesterol or DOPE can maximize transgene expression in vivo. For example, mixing cholesterol instead of DOPE with DOTAP, DOTMA, or DDAB may substantially increase transgene expression in vivo.

Particular cells within the lung may be targeted by modifying the liposomes to direct them to particular types of cells using site-directing molecules. Thus antibodies or ligands for particular receptors may be employed, to target a cell associated with a particular surface protein. A particular ligand or antibody may be conjugated to the liposome in accordance with conventional ways, either by conjugating the site-directing molecule to a lipid for incorporation into the lipid bilayer or by providing for a linking group on a lipid present in the bilayer for lining to a functionality of the site-directing compound. Such techniques are well known to those skilled in the art. For example, ligand-directed DNA-polycation complexes have been shown transfect to hepatocytes in the liver after iv injection.

Non-cationic liposomes, particularly pH sensitive liposomes, offer another potentially attractive approach to in vivo gene therapy. However, as compared to cationic liposomes, pH sensitive liposomes are less efficient in capturing DNA and delivering DNA intracellularly. Anionic and neutral liposomes are readily available, such as from Avanti Polar Lipids (Birmingham, Ala.), or can be easily prepared using readily available materials. Such materials include phosphatidylcholine, cholesterol, phosphatidylethanolamine, dioleoylphosphatidylcholine (DOPC), dioleoylphoshatidylethanolamine(DOPE), among others. These materials can also be mixed with the DOTMA and DOTAP starting materials in appropriate ratios. Methods for making liposomes using these materials are well known in the art.

Unexpectedly, the liposomal lipid composition of the liposomes used for nebulization can dramatically affect the level of transgene expression produced in vivo. Thus, the liposomal lipid compositions generally have a composition of 50% molar ratio of cationic lipid to non-cationic lipid, but may range from 5% to 100%. The diameter of the liposomes should generally be within the range of 100 nm to 10 microns, preferably 100 nm to 500 nm. Other DNA sequences, such as adenovirus VA genes can be included in the liposome-DNA complex formulation or be co-transfected with the gene of interest. The presence of genes coding for the adenovirus VA gene product may significantly enhance the translation of mRNA transcribed from the plasmid.

The liposomes can comprise multilamellar vesicles (MLVs), small unilamellar vesicles (SUVs), or large unilamellar vesicles (LUVs). MLV and LUV are prepared by vortexing rather than sonicating after addition of the aqueous material to the dry lipid film. If desired, the resulting liposomes can be extruded under high pressure through sized polycarbonate membranes to achieve more uniform size distributions. SUVs are prepared by extended sonication of MLVs to produce a homogeneous population of unilamellar liposomes. Commonly used methods for making liposomes include $Ca^{2+}$-EDTA chelation (Papahadjopoulos, et al., *Biochim. Biophys. Acta* (1975) 394:483; Wilson, et al., *Cell* (1979) 17:77); ether injection (Deamer, D. and Bangham, A., *Biochim. Biophys. Acta* (1976) 443:629; Ostro, et al., *Biochem. Biophys. Res. Commun.* (1977) 76:836; Fraley, et al., *Proc. Natl. Acad. Sci. USA* (1979) 76:3348); detergent dialysis (Enoch, H. and Strittmatter, P., *Proc. Natl. Acad. Sci. USA* (1979) 76:145) and reverse-phase evaporation (REV) (Fraley, et al., *J. Biol. Chem.* (1980) 255:10431; Szoka, F. and Papahadjopoulos, D., *Proc. Natl. Acad. Sci. USA* (1978) 75:145; Schaefer-Ridder, et al., *Science* (1982) 215:166).

The various liposome-nucleic acid complexes are prepared using methods well known in the art. See, e.g., Straubinger et al., in *Methods of Immunology* (1983), Vol. 101, pp. 512–527. By "liposome-nucleic acid complex" is meant a nucleic acid sequence as described above, either bound to the surface of, or entrapped in, a liposome preparation, as discussed below. The liposome preparation can also contain other substances, such as enzymes necessary for transcription and translation, cofactors, etc. Furthermore, the liposome-nucleic acid complex can include targeting agents to deliver the complex to particular cell or tissue types. MLVs containing nucleic acid can be prepared by depositing a thin firm of phospholipid on the walls of a glass tube and subsequently hydrating with a solution of the material to be encapsulated and vortexing. The nucleic acid material is added to a suspension of preformed MLVs or SLVs only after the liposomes have been prepared and then vortexed. When using liposomes containing cationic lipids, the dried lipid film is resuspended in an appropriate solution such as sterile water or an isotonic buffer solution such as 10 mM Tris/NaCl, or 5% dextrose in sterile water, sonicated, and then the preformed liposomes are mixed directly with the DNA. The liposome and DNA form a very stable complex due to binding of the negatively charged DNA to the cationic liposomes. SUVs find use with small nucleic acid fragments as well as large regions of DNA (>250 kb).

In preparing the liposome-nucleic acid complex, care should be taken to exclude any compounds from the solution which may promote the formation of aggregates of the liposome-nucleic acid complexes. Large particles generally will not be aerosolized by the nebulizer and even if aerosolized would be too large to penetrate beyond the large airways. Aggregation of the liposome-nucleic acid complex is prevented by controlling the ratio of DNA to liposome, minimizing the overall concentration of DNA:liposome complex in solution, usually less than 5 mg DNA/8 ml solution, and avoiding chelating agents such as EDTA, and significant amounts of salt which tend to promote macro-aggregation. The preferred excipient is water, dextrose/water or another solution having low or no ionic strength. Further, the volume must be adjusted to the minimum for deposition in the lungs of the host mammal, but taking care not to make the solution too concentrated so that aggregates form.

The choice of liposomes and the concentration of liposome-nucleic acid complexes thus involves a two step process. The first step is to identify liposomes and concentration of liposome-nucleic acid complexes that do not aggregate when the components are combined or during the significant agitation of the mixture that occurs during the nebulization step. The second step is to identify among those that are identified as of interest at the first step (i.e. do not aggregate) those complexes that provide for a high level of transfection and expression of a gene of interest in target cells in the lung. The level of expression and the cell types in which expression of the recombinant gene is obtained may be determined at the mRNA level and/or at the level of polypeptide or protein. Gene product may be quantitated by measuring its biological activity in tissues. For example, enzymatic activity can be measured by biological assay or by identifying the gene product in transfected cells by immunostaining techniques such as probing with an antibody which specifically recognizes the gene product or a reported gene product present in the expression cassette.

As an example, a reporter gene CAT (which encodes chloramphenicol acetyl transferase) can be inserted in the expression cassette and used to evaluate each liposome composition of interest. The DNA:liposome complexes must be mixed in solutions which do not themselves induce aggregation of the DNA:liposome complexes such as sterile water. The expression cassette (DNA) is mixed together with the liposomes to be tested in multiple different ratios, ranging as an example from 4:1 to 1:10 (micrograms DNA to nanomoles cationic lipid). The results will provide information concerning which ratios result in aggregation of the DNA:liposome complexes and are therefore not useful for use in vivo, and which complexes remain in a form suitable for aerosolization. The ratios which do not result in aggregation are tested in animal models to determine which of the DNA:liposome ratios confer the highest level of transgene expression in vivo. For example, the optimal DNA:liposome ratios for SUV for DOTMA/DOPE and DDAB:Chol are 1:1 or 1:2.

Administration

The mammalian host may be any mammal having symptoms of a genetically-based disorder. Thus, the subject application finds use in humans, domestic animals, feed stock, such as bovine, ovine, and porcine, as well as primates, particularly humans. In the method of the invention, transformation in vivo is obtained by introducing a non-integrating therapeutic expression vector into the mammalian host complexed to liposomes, particularly cationic liposomes. For introduction into the mammalian host any physiologically acceptable medium may be employed for administering the DNA or liposomes, such as deionized water, 5% dextrose in water, and the like. Other components may be included in the formulation such as stabilizers, biocides, etc, providing that they meet the criteria outlined above, i.e. do not cause aggregation of the complexes. The various components listed above find extensive exemplification in the literature and need not be described in particular here.

The liposome-nucleic acid complex is aerosolized by any appropriate method. For use with humans or other primates, the aerosol will be generated by a medical nebulizer system which delivers the aerosol through a mouthpiece, facemask, etc. from which the subject can draw the aerosol into the lungs. Various nebulizers are known in the art and can be used in the method of the present invention. See, e.g., Boiarski, et al., U.S. Pat. No. 4,268,460; Lehmbeck, et al., U.S. Pat. No. 4,253,468; U.S. Pat. No. 4,046,146; Havstad, et al., U.S. Pat. No. 3,826,255; Knight, et al., U.S. Pat. No. 4,649,911; Bordoni, et al., U.S. Pat. No. 4,510,829. The selection of a nebulizer system will depend on whether alveolar or airway delivery (i.e., trachea, primary, secondary or testiary bronchi, etc.), is desired.

A convenient way to insure effective delivery of the nucleic acid to the alveoli is to select a nebulizer which produces sufficiently small particles (e.g., producing particles with a mean particle diameter of less than 5.0 microns ($\mu$m), more preferably having a mean particle diameter of about 0.2 to about 4.0 $\mu$m, and most preferably having a mean diameter of about 0.2 to about 2 $\mu$m), since the larger particles ($\geq$5 $\mu$m) are generally deposited in the proximal airways or nasopharynx. As an alternative to selecting small mean particle diameters to achieve substantial alveoli deposition, a very high dosage of the liposome-nucleic acid preparation can be administered, with a larger mean particle diameter. A proviso to such an approach is that the particular liposome-nucleic acid complex is not too irritating at the required dosage and that there are a sufficient number of particles in the total population having a diameter in the 0.5 to about 5 $\mu$m range to allow for deposition in the alveoli. For proximal airway delivery, the mean particle size will be larger. For example, suitable mean particle diameters will generally be less than about 15 $\mu$m, more preferably from about 4 $\mu$m, and most preferably from about 5 $\mu$m to about 10 $\mu$m.

Examples of nebulizers useful for alveolar delivery include the Acorn 1 nebulizer, and the Respirgard II™ Nebulizer System, both available commercially from Marquest Medical Products, Inc., Inglewood, Colo. Other commercially available nebulizers for use with the instant invention include the UltraVent™. nebulizer available from Mallinckrodt, Inc. (Maryland Heights, Mo.); the Wright nebulizer (Wright, B. M., *Lancet* (1958) 3:24–25); and the DeVilbiss nebulizer (Mercer et al., *Am. Ind. HYR. Assoc. J.* (1968) 29:66–78; T. T. Mercer, Chest (1981) 80:6 (Sup) 813–817). Nebulizers useful for airway delivery include those typically used in the treatment of asthma. Such nebulizers are also commercially available. One of skill in the art can determine the usefulness of a particular nebulizer by measuring the mean particle size generated thereby with e.g. a 7 stage Mercer cascade impactor (Intox Products, Albuquerque, N. Mex.). Concentrations of the liposome-nucleic acid complex from the impactor plates can be determined by eluting the complex therefrom and assessing the optical density at an appropriate wavelength and comparing the standard curves. Results are generally expressed as mass median aerodynamic diameter±geometric standard deviation (Raabe, *J. Aerosol Sci.* (1971) 2:289–303).

The amount of liposomes used will be sufficient to provide for adequate transfection after entry of the DNA or complexes into the lung and to provide for a therapeutic level of expression in transfected cells. A therapeutic level of expression is a sufficient amount of expression to treat or palliate a disease of the host mammal following administration of an effective amount of the liposome-nucleic acid complex to the host mammal's lung, particularly the alveoli or airway. Thus, an "effective amount" of the aerosolized liposome-nucleic acid preparation, is a dose sufficient to effect treatment, that is, to cause alleviation or reduction of symptoms, to inhibit the worsening of symptoms, to prevent the onset of symptoms, and the like. The dosages of the present compositions which will constitute an effective amount can be determined in view of this disclosure by one of ordinary skill in the art by running routine trials with appropriate controls. Comparison of the appropriate treatment groups to the controls will indicate whether a particular dosage is effective in preventing or reducing particular symptoms. Appropriate doses are discussed further below. While there is no direct method of measuring the amount of liposome-nucleic acid complex delivered to the alveoli, bronchoalveolar lavage (BAL) can be used to indirectly measure alveolar concentrations of the expressed protein, usually 18–24 hrs after inhalation to allow clearance of the protein deposited in the larger airways and bronchi.

The total amount of the nucleic acid delivered to mammalian host will depend upon many factors, including the total amount aerosolized, the type of nebulizer, the particle size, subject breathing patterns, severity of lung disease, concentration and the mean diameter of the liposome-nucleic acid complex in the aerosolized solution, and length of inhalation therapy. Thus, the amount of expressed protein measured in the alveoli may be substantially less than what would be expected to be expressed from the amount of nucleic acid present in the aerosol, since a large portion of the complex may be exhaled by the subject or trapped on the interior surfaces of the nebulizer apparatus. For example, approximately one third of the dose that is placed into the nebulizer remains in the nebulizer after inhalation is completed. This is true regardless of the dose size, duration of inhalation, and type of nebulizer used. Moreover, resuspension of the residue and readministration does not significantly increase the dose delivered to the subject; about one third remains in the nebulizer. Furthermore, even with minimization of airway deposition, there is a portion which is still deposited in the airways. Additionally, efficiency of expression of the encoded protein will vary widely with the expression system used.

Despite these interacting factors, one of ordinary skill in the art will be able to readily design effective protocols, particularly if the particle size of the aerosol is optimized. Based on estimates of nebulizer efficiency, an effective dose delivered will usually lie in the range of about I mg/treatment to about 500 mg/treatment, although more or less may be found to be effective depending on the subject and desired result. It is generally desirable to administer higher doses when treating more severe conditions. Typically, the therapeutic cassette is not integrated into the host cell genome. If necessary, the treatment can be repeated on an ad hoc basis depending upon the results achieved. If the treatment is repeated, the mammalian host can be monitored to ensure that there is no adverse immune response to the treatment. The frequency of treatments depends upon a number of factors, such as the amount of liposome-nucleic acid complex administered per dose, as well as the health and history of the subject. As used herein, with reference to dosages, "liposome-nucleic acid aerosol" refers to the amount of liposome-nucleic acid complex that is placed in the nebulizer and subjected to aerosolization. The "amount nebulized" or "amount aerosolized" of the complex means the amount that actually leaves the apparatus as an aerosol, i.e., the amount placed into the apparatus less the amount retained in the reservoir and on the inner surfaces of the apparatus at the conclusion of a treatment session.

In general, in the treatment of cancer, it will usually be necessary to administer sequential doses at intervals ranging from every 8 to 12 hours to once a month, until significant amelioration or complete disappearance of the cancer results, or until dose limiting host toxicity develops. Similar administration protocols may also be used in e.g. patients where all macroscopic evidence of tumor has been removed, in order to prevent tumor recurrence due to persistence of undetected microscopic disease. To treat pulmonary infections such as bronchitis and pneumonia, it will usually be necessary to administer at least one dose per day over a period of about 4 to about 21 consecutive days or longer. The treatment is usually carried out on consecutive days because new areas of the lungs open up to penetration and deposition of the nucleic acid with increasing resolution of the infection. The success of the treatment can be monitored and the administration regimen altered by assessing conventional clinical criteria; e.g., clearing of radiographic infiltrate, improved arterial $PO_2$ (e.g., >70 mmHg), reduction in dyspnea, respiratory rate and/or fever. For the treatment of genetic disorders, such as cystic fibrosis, the liposome-nucleic acid complex will be administered at regular intervals, from once a week to once every one to several months, in order to replace the normal CRTR protein in critical host airway cells, since these cells continue to turn over. It may also be possible to stably transfect the CMTR gene into appropriate lung stem cells, which would then provide a continuous source of normal airway cells without requiring lifelong treatment. Potential therapeutic effects of the gene product can be measured, by determining the effects of gene expression on survival of transgenic host mammals in which the transgene is expressed. Production of significant amounts of a transgene product will substantially prolong the survival of the affiliated host.

Where expression of the polypeptide/protein or even the mRNA itself confers a changed biochemical phenotype upon the host, the presence of a new phenotype or absence of an old phenotype may be evaluated; for example, as a result of transformation of the host cells, there may be enhanced production of pre-existing desirable products formerly produced in insufficient quantities or there may be reduction or even suppression of an undesirable gene product using antisense, ribozyme or co-suppression technologies; in the case of suppression, a reduction of the gene product may be determined.

The potential toxicity of the treatment may be evaluated both by behavioral manifestations, and where appropriate by analysis of biopsy specimens. Thus, behavioral activity which evidences distress, such as activity level, changes in eating and dining patterns and the like can be monitored, as well as evidence of neurosis, edema or inflammation in biopsy specimens.

The subject compositions can be provided for use in one or more procedures. Kits will usually include the DNA either as naked DNA or complexed to liposomes. Additionally, liposomes may be provided in a separate container for complexing with the provided DNA. The DNA or the liposome/DNA complexes may be present as concentrates which may be further diluted prior to use or they may be provided at the concentration of use, where the vials may include one or more dosages. Conveniently, single dosages may be provided in sterilized containers suitable for use with a nebulizer, so that the physician or veterinarian may employ the containers directly with a nebulizer, where the containers will have the desired amount and concentration of agents. Thus, the kit may have a plurality of containers containing the DNA or the DNA/liposome complexes in appropriate proportional amounts. When the containers contain the formulation for direct use, usually there will be no need for other reagents for use with the method.

Uses of the subject invention include but are not limited to the following. The present invention is particularly useful for the delivery of substances directly into the lung for the prevention and/or treatment of pulmonary disorders such as lung cancer, emphysema, asthma, lung infections such as chronic bronchitis and pneumonia, degenerative diseases of the lung, as well as genetic disorders such as cystic fibrosis and α-1 antitrypsin deficiency.

For the treatment of lung tumors, genes encoding toxic peptides (i.e. chemotherapeutic agents such as ricin, diphtheria toxin and cobra venom factor), tumor suppressor genes such as p53, genes coding for mRNA sequences which are antisense to transforming oncogenes, or other antineoplastic peptides, such as tumor necrosis factor (TNF) and other cytokines, or transdominant negative mutants of transforming oncogenes, can be inserted into the expression vector and using the above described methods, complexed delivered for expression at or near the tumor site. Such tumors can be specifically targeted by incorporating targeting agents, such as antibodies directed against tumor cell surface antigens, onto the liposomal surface. See, e.g., Laserman, et al., *Nature* (1980) 288:602–604; Huang, et al., *Biochemisty* (1981) 20:4299–4238, for methods of incorporating antibodies onto liposomal surfaces. Similarly, genes coding for peptides known to display antiviral and/or antibacterial activity, or stimulate the host immune system, can also be administered to the lung in order to treat pulmonary infections. Thus, the genes encoding many of the various cytokines (or functional fragments thereof, such as the interleukins, interferons, and colony stimulating factors, will find use with the instant invention. The gene sequences for a number of these substances are known. Interferon-y produces significant anti-pneumocystis carinii pneumonial (PCP) activity in immunodeficient mice with PCP following aerosol delivery of the peptide. Beck et al., *Infect. and Immun.* (1991) 59:3859–3862.

Genes encoding antioxidants will also find use for the treatment or prevention of lung damage due to degenerative lung disorders caused by smoking and other environmental agents. For example, genes encoding superoxide dismutase (SOD) or catalase, as well as α-1 antitrypsin, will be particularly useful for this purpose. These gene sequences are known. See, e.g., Long et al., *Biochem*, (1984) 23:4828–4837 for the α-1 antitrypsin gene sequence. For the treatment of genetic disorders, such as cystic fibrosis and emphysema, functional genes, corresponding to genes known to be deficient in the particular disorder, can be administered to the subject. For example, it is known that individuals lacking sufficient levels of α-1 antitrypsin are prone to emphysema and other pulmonary disorders. Thus, this gene can be administered prophylactically, as well as in response to clinical manifestations of the disease, for both the prevention and/or treatment of this disorder. Similarly, the gene involved in cystic fibrosis has been identified. Goodfellow, P., *Nature* (1989) 341:102–103; Rommens, et al., *Science* (1989) 245:1059–1054; Beardsley, et al., *Sci. Am.* (1989) 261:28–30. Thus, this gene, or functional fragments thereof, can be delivered to subjects in order to treat this disorder.

The invention also finds use for the delivery of substances into the systematic circulation via the lung. For example, as explained above, a number of substances, such as cytokines, are toxic when administered using conventional methods of delivery. See, e.g., Debs et al., *J. Immunol* (1988) 140:3482–3488. The invention allows the delivery of these substances, e.g., in order to fight cancer, as well as bacterial and viral infection, systemically. This approach has already shown promise for the treatment of extra-pulmonary cancer in humans. This method of transfecting lung cells also avoids exposure of host mammal gonads thus avoiding transfection of germ cells.

The instant methods will also find use in antisense therapy, for the delivery of oligonucleotides able to hybridize to specific complementary sequences, thereby inhibiting the transcription and/or translation of these sequences. Thus, DNA or RNA coding for proteins necessary for the progress of a particular disease, can be targeted, thereby disrupting the disease process. For a review of antisense therapy and oligonucleotides useful in the same, see, Uhlmann, E. and Peyman, A., *Chem. Rev.* (1990) 90:543–584.

The following examples are provided for illustrative purposes only and are not meant to limit the scope of the present invention.

EXAMPLES

The practice of the present invention employs unless otherwise indicated, conventional techniques of cell culture, molecular biology, microbiology, recombinant DNA, and immunology, which are within the skill of the art. Such techniques are explained fully in the literature. See, e.g., Sambrook, et al., Molecular Cloning: A Laboratory Manual, Second Edition (1989) Vols. 1–3; DNA Cloning (1985) Vols. I and II, D. N. Glover (ed.); Nucleic Acid Hybridization (1984), B. D. Hames, et al., (eds.); Perbal, B., A Practical Guide to Molecular Cloning (1984); Methods in Enzymology (the series), Academic Press, Inc.; Vectors: A Survey of Molecular Cloning Vectors and Their Uses (1987), R. L. Rodriguez, et al., (eds.), Butterworths; and Miller, J. H., et al., Experiments in Molecular Genetics (1972) Cold Spring Harbor Laboratory.

Example I

Expression of chloramphenicol acetyltransferase (CAT) gene, in rodent lungs following aerosolized delivery of liposome-nucleic acid complexes.

The vectors used were plasmid pRSV-CAT, as described by Gorman, et al., *Proc. Natl. Acad. Sci. USA* (1982) 79:6777–6781; and Juang, and Gorman, *Mol. Cell. Biol.* (1990) 10:1805–1810; a plasmid containing the CAT gene driven by the RSV long terminal repeat; and plasmid pRSV-p-gal, as described by Hazinski et al., *Am. J. Respir. Cell Mol. Biol.* (1991) 4:206–209.

The pRSV-CAT plasmid was complexed to liposomes and administered to rodent subjects as follows. Two mg. of pRSV-CAT was mixed with 4 μmoles of DOTMA (GIBCO BRL, Grand Island, N.Y.)/cholesterol (2:1) small unilamellar liposomes in phosphate buffered saline and then nebulized in an Acorn I nebulizer (Marquest Medical Products, Inc., Inglewood, Colo.) to groups of rats or mice in an Intox nose only exposure chamber (intox Products, Albuquerque, N.M.). The same procedure was followed with 0.5 mg pRSV-CAT mixed with 1.0 μmol DOTMA-cholesterol, as well as 2.0 mg pRSV-CAT alone. Two to five days later, animals were sacrificed and lungs collected. Lungs were also collected from untreated controls. The lungs were homogenized and cells disrupted with three freeze-thaw cycles. CAT activity in aliquots from these lung extracts was measured using a standard assay as described by Wolff, et al., Science (1990) 247:1465–1468. As can be seen in FIG.

1, animals administered 2.0 mg RSV-CAT with 4.0 μmol DOTMA/cholesterol expressed the CAT protein while the control animals did not. A similar procedure was followed with respect to pRSV-β-gal, with the exception that 50 mg. of pRSV-β-gal was mixed with 50 μmoles of DOTMA/cholesterol (2:1). The presence of β-gal activity was determined using a standard histochemical staining procedure. β-gal activity was present in the airway epithelial cells of exposed rats.

Also tested was a plasmid containing the CAT gene driven by the CMV promoter. This vector was made as described in Huang, M. T. F. and Gorman, C. M. *Nuc. Acids Res.* (1990) 18:937–947, with the exception that the CMV promoter and a hybrid intron sequence were used rather than the SV40 promoter in the plasmid pML.I.CAT, described therein. Briefly, the CAT vector was constructed by first making a pML-based plasmid containing the CMV promoter immediately followed by a portion of the 5'-untranslated leader from the adenovirus-major late (AML) region. This region contained all but the first 13 nucleotides of the first exon of the tripartite leader plus a portion of an intervening sequence (IVS) from the AML region. A synthetic oligonucleotide was inserted which merged with the adenovirus intron to provide a functional splice acceptor sequence derived from an IgG variable region. Bothwell, et al, *Cell* (1981) 24:625–637. This vector was then cut at two restriction sites bordering the intron (ClaI and PstI) to remove a 292 bp fragment. A matching synthetic oligonucleotide linker was inserted. The plasmid was termed pCIS-CAT.

Figure 2:
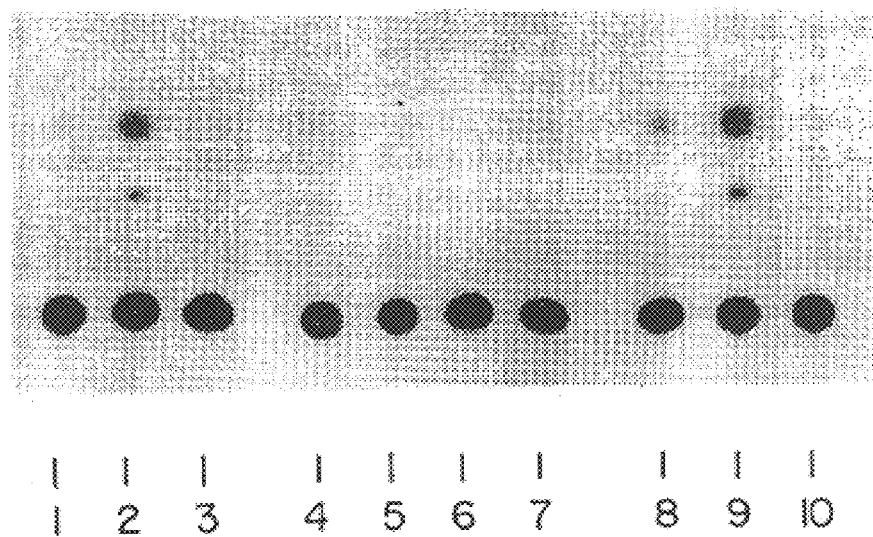

To test for expression of the CAT gene using pCIS-CAT, 12 mg pCIS-CAT was mixed with 24 μmoles of DOTMA/DOPE. Female ICR mice were placed in three different aerosol receiving chambers. All mice received the same amount of the CAT expression plasmid complexed to liposomes, as described above. Animals 1–3 were exposed to the aerosol in an Intox designed aerosol chamber. Animals 4–7 were exposed to the aerosol in a modified rat cage containing dividers for individual mice. Animals 8–10 were placed in a smaller, similarly modified mouse cage after being put in the restrainers used in the Intox chamber. 48 hours following aerosolization, the animals were sacrificed and whole lungs assayed for CAT expression using the chromatographic CAT assay. As can be seen in FIG. 2, a single aerosol dose of a CAT gene-expression plasmid complexed to cationic liposomes can produce high-level transgene expression in the lungs of mice. Significant levels of transgene expression are present in the lungs of all 7 mice (numbers 1–3 and 8–10) which were exposed to the aerosol mist in Intox nose-only exposure tubes which were constructed to maximize the amount of aerosol that the mice inhaled. The amount of variation seen here is comparable to that seen in other aerosol experiments and may have several explanations, including variations in exposure to the aerosol mist, individual variations in efficiency of nasal filtration, etc.

Example II

Animals

Two month old, female, ICR mice were used in all experiments.

Preparation of plasmid DNA

We have used the chloramphenicol acetyltransferase (CAT) gene as a reporter to measure transgene expression levels (Gorman et al., *Proc. Nat'l Acad Sci* (USA) (1982) 79: 6777–6781). The plasmid vector used contains the CAT gene fused to the human cytomegalovirus (CMV) immediate early promoter-enhancer element (pCIS-CAT). The plasmid was purified using alkaline lysis and ammonium acetate precipitation (Sambrook et al. (1989) supra), and the nucleic acid concentration measured by UV absorption at 260 nm. The CAT gene is not present in eukaryotic cells. Its product is an enzyme which catalyzes the transfer of acetyl groups from acetylCoA to the substrate chloramphenicol.

Preparation of cationic liposomes

Liposomes were prepared as small unilamellar vesicles (approximately 100 nm in diameter) containing the cationic lipid DOTMA as DOTMA:DOPE (1:1 mole ratio). DOTMA is (N[1-2,3-dioleyloxy)propyl]-N,N,N-triethylammonium (Syntex Corporation), and DOPE is the neutral lipid dioleoylphosphatidylethanolamine (Avanti Polar Lipids). Stock solutions of the lipids were dissolved in chloroform and stored under argon at −20° C. Lipids were mixed in a round-bottomed flask and evaporated to dryness on a rotary evaporator under reduced pressure. Double distilled water was added to produce final lipid concentrations of 10 mM each, and the resulting mix was sonicated for approximately 20 minutes in a bath sonicator (Laboratory Supplies, Hicksville, N.Y.). The liposomes were stored under argon at 4° C. until use.

Aerosol delivery of plasmid/liposome complexes to mice

Twelve mg of plasmid complexed to 24 μmols of DOTMA:DOPE liposomes was aerosolized and administered to mice over two different aerosol periods on the same day. In order to prevent aggregation and precipitation of the oppositely charged components, the plasmid and the liposomes were diluted separately in sterile water prior to mixing. Six mg of plasmid DNA and 12 μmols of DOTMA:DOPE liposomes were each diluted to 8 ml with water and mixed. Equal volumes were then placed into two Acorn I nebulizers (Marquest, Englewood, Colo.), the animals placed into an Intox small animal exposure chamber (Albuquerque, N.M.), and an air flow rate of 4 L min$^{-1}$ used to generate the aerosol. Approximately 90 minutes were required to aerosolize this volume. The animals were removed from the chamber for 1–2 hours and then the above procedure was repeated.

Radiometric Assay of CAT Activity

Organs were dissected from sacrificed animals at periods from 1 to 21 days following aerosolization, washed in cold phosphate buffered saline (PBS), and homogenized using a hand-held tissue homogenizer in 250 mM Tris-HCl, pH. 7.5, 5 mM EDTA for lungs and spleen and 250 mM Tris-HCl, pH. 7.5,5 MM EDTA plus the protease inhibitors aprotinin, E-64, and leupeptic (Boehringer Mannheim) for liver, heart and kidneys. These inhibitors prevent degradation of acetylated chloramphenicol species generated during the assay, thereby allowing optimal detection of CAT expression.

Following homogenization, cells were lysed by three freeze/thaw cycles, the lysate heated (65° C. for 10 minutes), and centrifugated (16,000×g, 2 minutes). The protein concentrations of the extracts were measured using a Coomassie blue-based assay (Bio-Rad). Protein concentrations were normalized and a volume of extract added to 10 μl of 100 mM acetylCoA (Sigma), 0.3 μCi of [$^{14}$C]-labelled chloramphenicol (Amersham), and distilled water to a final volume of 180 μl, and allowed to react at 37° C. for 8–10 hours (Gorman et al. (1982) supra). Following the reaction, the acetylated and unacetylated chloramphenicol species were extracted with cold ethyl acetate, spotted on silica TLC plates, and developed with a chloroform:methanol (95:5v/v) solvent. The TLC plates were exposed to photographic film (Kodak X-OMAT) for one to three days.

Preparation of Genomic DNA and Southern Hybridization

Immediately following aerosolization, mice were sacrificed and their lungs removed. Genomic DNA was isolated and analyzed by Southern hybridization (Sambrook et al. (1989) supra) using a Hybond N+ membrane (Amersham). CAT probe was prepared from a 1.6 kb fragment of the CAT gene labelled with α-[$^{32}$P]dATP by random priming, which yielded a probe with an approximate specific activity of $2 \times 10^9$ dpm/μg. After hybridization, the membrane was washed three times in 2×SSC, 0.1% SDS at 65° C. for 20 minutes and exposed to film for 24 hours. In order to determine the approximate transfected CAT gene copy number, blots were also hybridized with a 1.1 kb BSU 36-1 single copy probe from a mouse factor VIII-A genomic clone (Levinson et al., *Genomics* (1992) 13: 862–865). Relative amounts of the CAT plasmid deposited in individual mouse lungs were quantitated by phosphorimagining analysis using a Molecular dynamics 400A phosphorimaginer (Johnson et al., *Electrophoresis* (1990) 11: 355–360). The amount of retained probe in each lane following hybridization with the CAT probe was normalized to the amount of DNA loaded per lane using the counts measured after hybridization with a FVIII-A single copy probe.

In Situ Inmunochemical Staining for CAT enzyme

At selected time points following aerosolization, mice were sacrificed and their lungs immediately removed. The lungs were slowly inflated with phosphate buffered saline (PBS) containing 33% by volume OCT (Miles, Inc.), placed in a tissue cassette filled with OCT, and frozen in 2-methylbutane chilled in a dry ice/ethanol bath. Cryosections were cut at 5 μm and collected onto salinized slides. CAT was detected after fixation of cryosections for 10 minutes in either 4% acetone or 2% paraformaldehyde in PBS containing 0.1% Tween 20 (PBST). All subsequent dilutions and washes were also done in PBST.

Following fixation, sections were washed three times (5 minutes each) then covered with 10% normal rabbit serum for 10 minutes at 20° C. The serum was replaced with diluted (1:500) rabbit polyclonal antibody against CAT (Drs. Parker Antin and David Standring, UCSF Medical Center). The antibody covered section was gently overlaid with a siliconized coverslip and incubated in a humid chamber at 4° C. for 24 hours. Slides were then warmed to 20° C. and washed three times. The presence of bound rabbit antibody against CAT was detected by covering sections with biotinylated, affinity purified, goat anti-rabbit antibody (Vector Laboratories) diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromagen, with endogenous alkaline phosphatase being inhibited with levamisole (Zymed). To control for potential spurious adherence of the streptavidin conjugate to bronchiolar epithelium, some sections were treated with free avidin and biotin prior to application of the primary antibody. Other controls, run concurrently, included the use of normal rabbit serum in place of primary antibody and the use of lung tissue from untreated mice.

Results

Initially, mice were exposed either to an aerosol generated from a solution containing 12 mg of a CMV-CAT expression plasmid alone or to an aerosol generated from a solution containing 12 mg of CMV-CAT complexed to 24 μmoles of DOTMA:DOPE (1:1) liposomes. Aerosols were administered to animals after they were placed individually in nose out cones and inserted into an Intox small animal exposure chamber. The mice showed no apparent ill effects or respiratory distress either during or after aerosol exposure. CAT assays taken from extracts of the lungs of mice sacrificed 72 hours following aerosol administration demonstrated that significant CAT gene expression was seen only in mice exposed to aerosolized DNA/liposome complexes.

How long CAT protein was present in the lungs of mice and whether expression of the reporter gene was limited to the lung was then investigated. Despite inter-animal variation, high levels of CAT activity are present for at least 21 days following a single aerosol dose of DNA/liposome complexes. No CAT activity was detectable in extracts from the heart, spleen, kidneys or liver of animals that showed high level expression in the lung, suggesting that the expression of the transgene was found to be lung-specific after aerosolization delivery of DNA-liposome complexes. This is consistent with prior observations showing that penetration of very high molecular weight substances through the respiratory epithelium of normal animals is very limited. Plasmid DNA/liposome complexes have molecular weights greater than $10^6$.

Although the small animal exposure chamber used in these experiments is designed to efficiently deliver a uniform aerosol dose to multiple animals, we have observed significant variations in the level of CAT activity in the lungs of mice within a single experiment were observed. One possible explanation for this variability is that the amount of DNA/liposome complex deposited in the lungs of mice is not uniform. In order to test this hypothesis, initial lung deposition of liposomes was measured using fluorescence analysis and of DNA was measured using Southern blot analysis. Either aerosolized cationic liposomes alone or DNA/liposome complexes containing 0.5 mole percent of a fluorescently labelled lipid, rhodamine-phosphatidylethanolamine were administered to mice.

Immediately following aerosolization, the animals were sacrificed and their lungs removed, homogenized and rhodamine fluorescence measured in a fluorimeter. The recovered fluorescence per animal was 0.06%±0.02 (S.D.) of the total amount aerosolized. This suggests than less than 10 μg out of the 12 mg of DNA aerosolized per experiment was actually deposited in the lung. In addition, there was no significant difference in lipid deposition between animals receiving liposomes alone and those receiving the DNA/liposome complexes. Since it is possible that a disruption of the complex could have occurred during nebulization, the amount of CAT gene deposited during aerosolization was also assessed. Immediately following aerosol delivery of DNA/liposome complexes, mice were sacrificed and total lung DNA prepared. Southern blots were probed with α[$^{32}$P]-labelled CAT gene. Labelled bands were scanned and demonstrated less than a 4-fold difference in plasmid deposition between animals in the same experiment. These results suggest that the mouse to mouse variation in CAT gene levels following aerosol delivery (up to ten-fold) is not only a function of the amount of complex initially deposited in the lung, but may also reflect differences in the site of uptake, rate of lung clearance, and/or variation in the ability of different lung cell types to express the transgene.

To determine the types and percentage of lung cells which were transfected in vivo, lungs of mice sacrificed 72 hours following exposure to an aerosol containing DNA/liposome complexes were cryosectioned, probed with a polyclonal anti-CAT antibody and counterstained to detect intracellular CAT protein. Lung sections taken from DNA/liposome treated mice had a diffuse immunostaining pattern involving bronchiolar and alveolar components. The bronchiolar epithelial cytoplasm stained with greatest intensity and uniformity. CAT antigen was detected (as demonstrated by red staining) in nearly all conducting airways with only rare individual or 2–3 cell clusters not staining. The diffuse alveolar pattern was due to moderately intense staining of the majority of alveolar lining cells. These areas occasionally faded into small, randomly scattered regions where lining cell staining was faint. Focal, intense staining (arrows) occurred in the cytoplasm of scattered, individual, alveolar lining cells. Controls included substitution of the primary antibody with normal rabbit serum and use of lung sections from untreated animals. Immunostaining was not recognized in either of the control preparations. Examination of multiple sections of lung from treated and control mice demonstrated no significant lesions.

Example III

High level airway expression of the human CFTR gene in mouse lungs after aerosol administration of DDAB:cholesterol liposome-pZN32 complexes Animals. Two months old, female, ICR mice obtained from Simonsen, Gilroy, CA., were used.

Figure 3A:
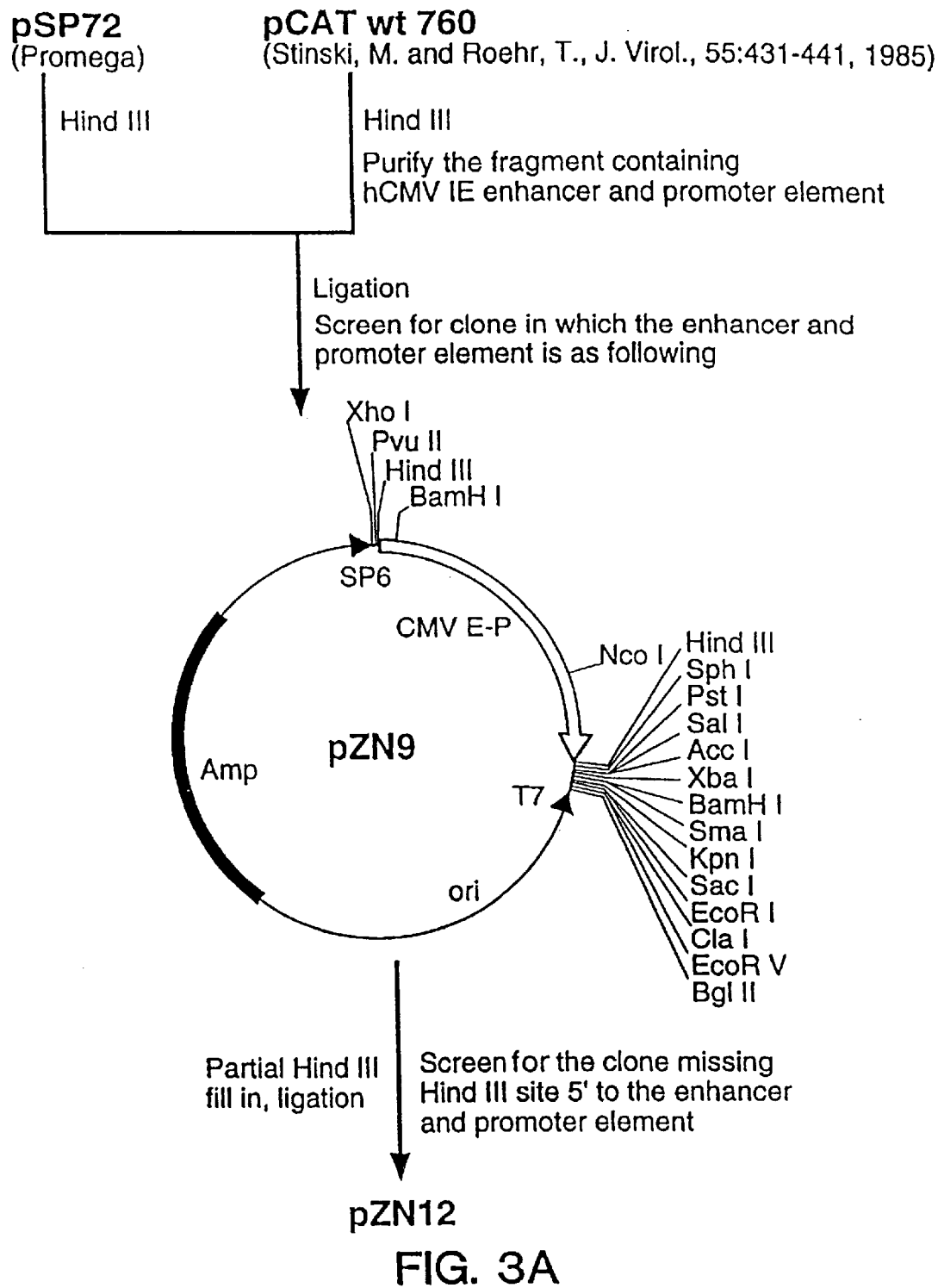
FIG. 3 shows construction of pZN13.
Figure 3B:
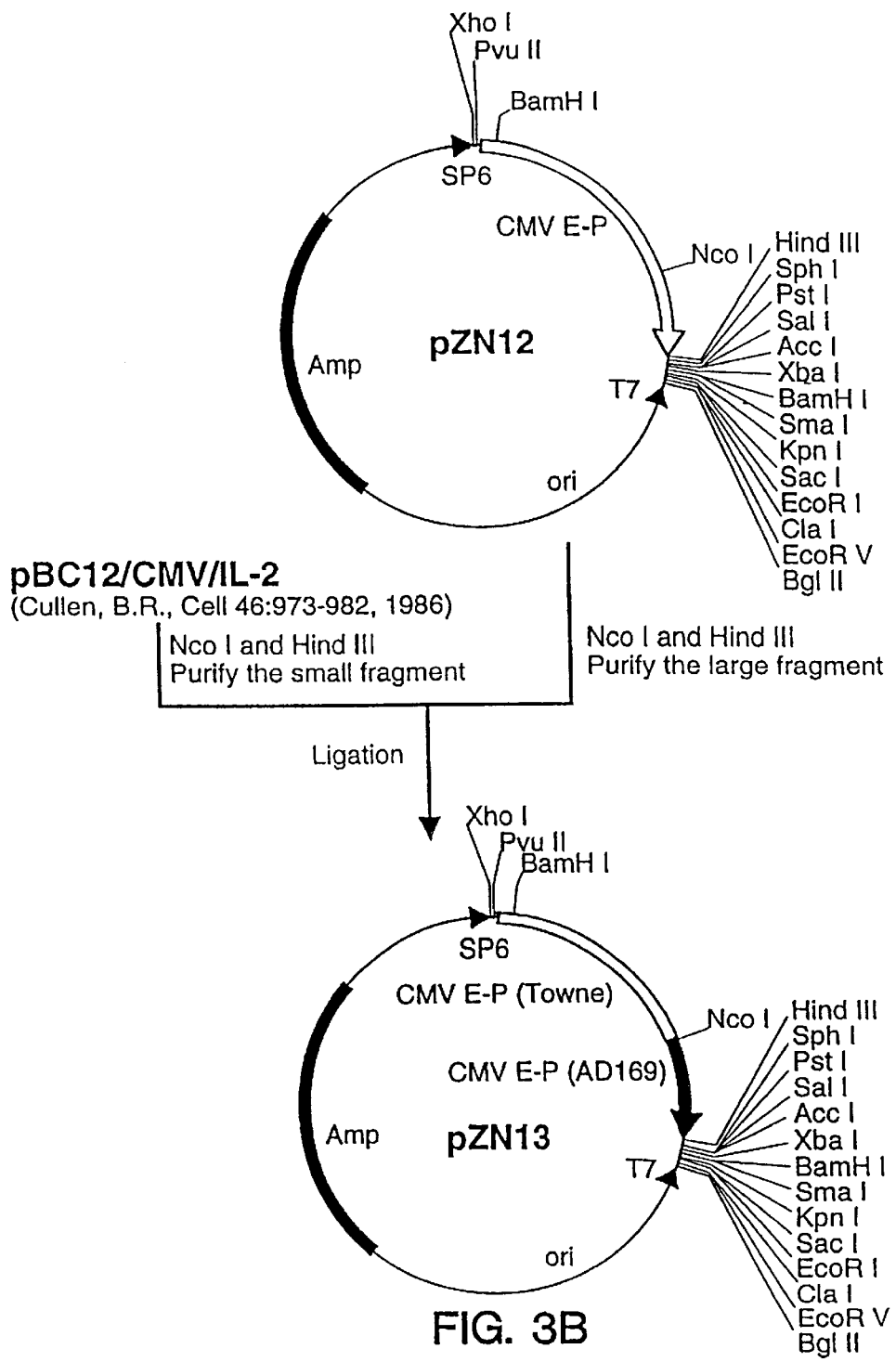
Figure 3C:
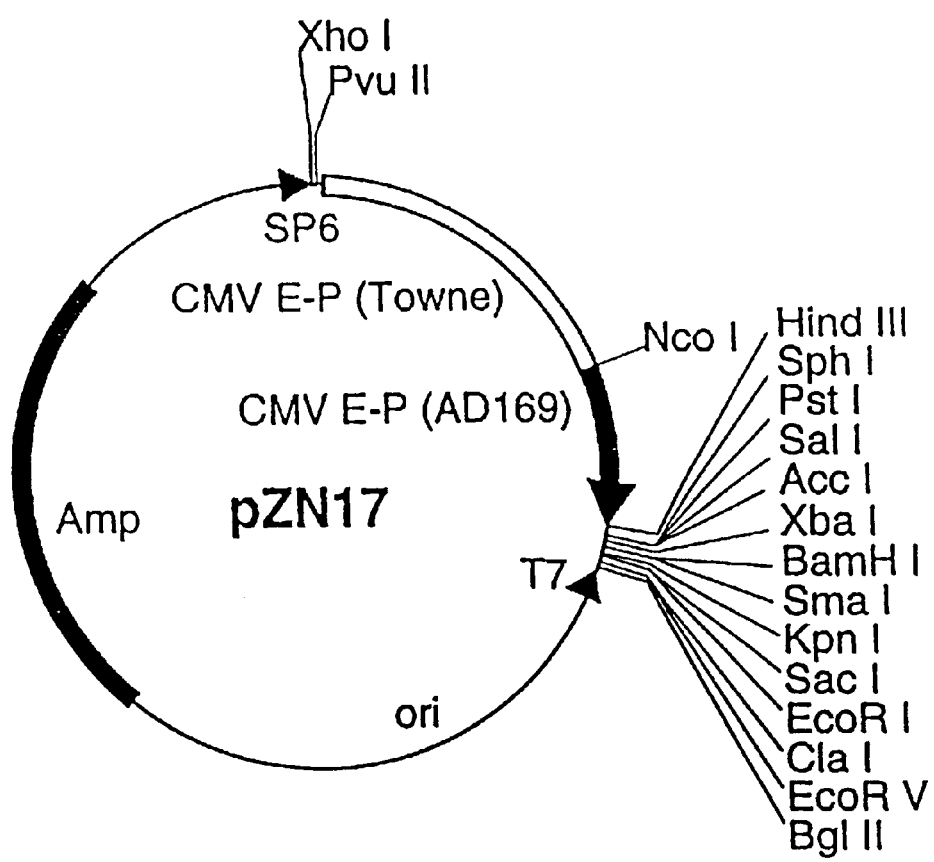
Figure 4A:
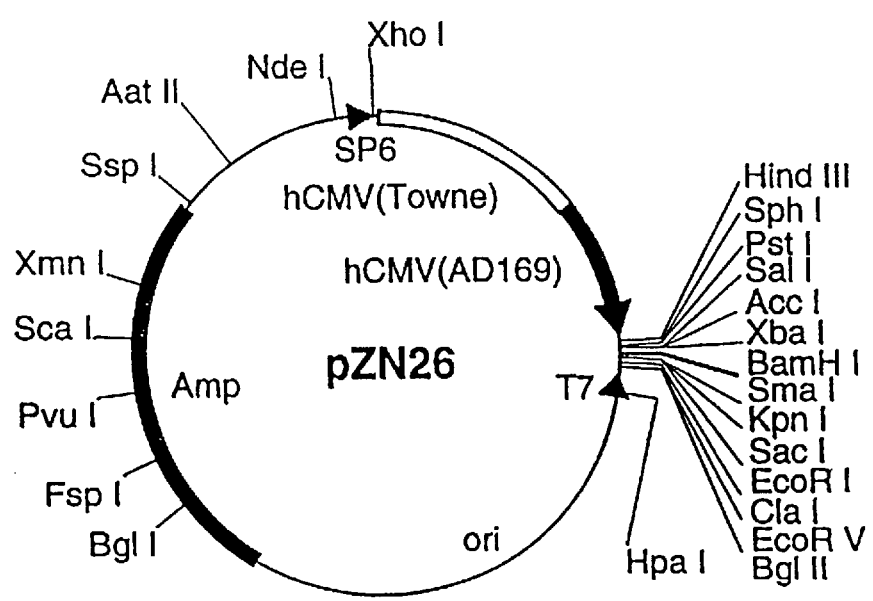
FIG. 4 shows construction of pZN29.
Figure 4B:
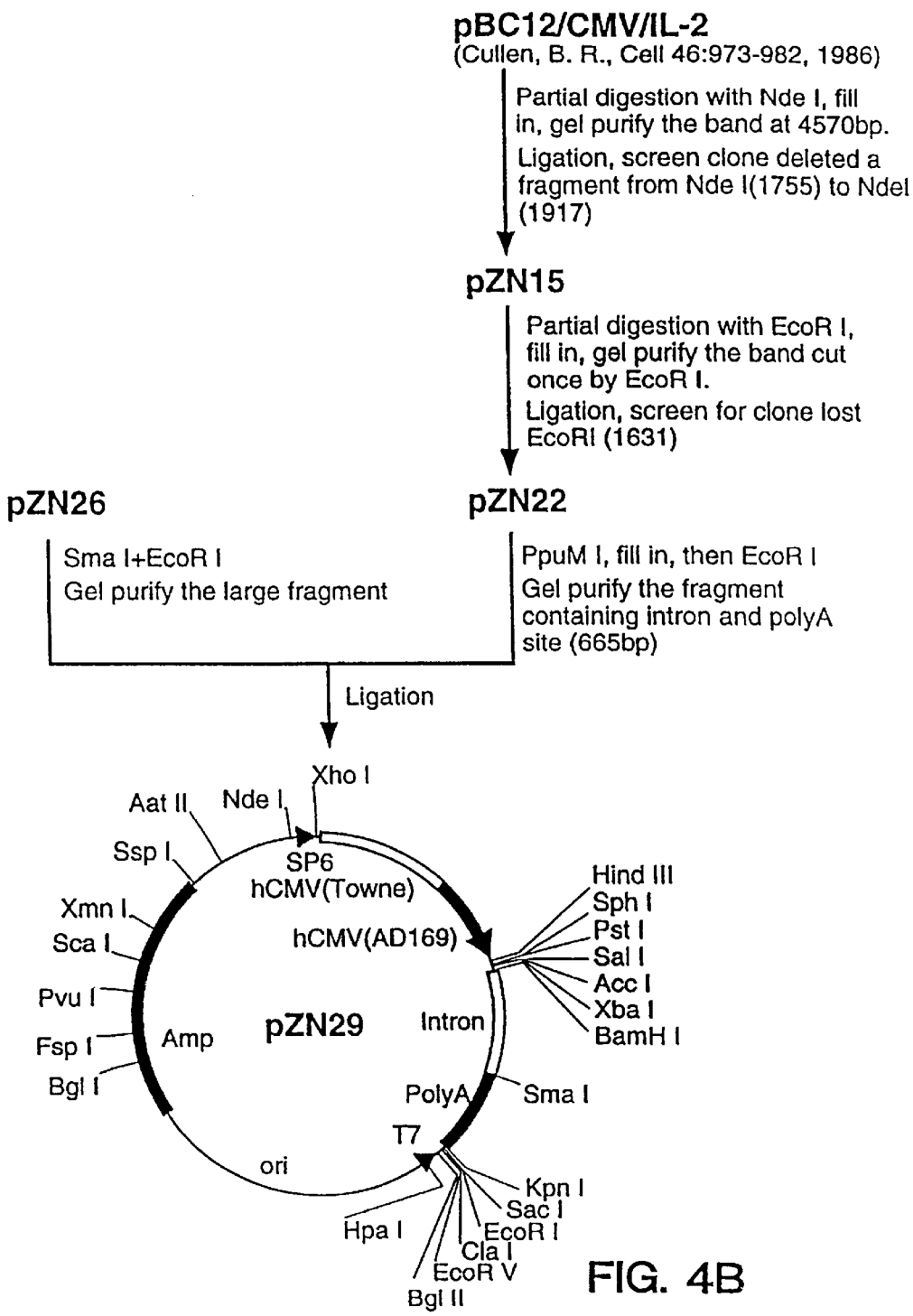
Figure 5:
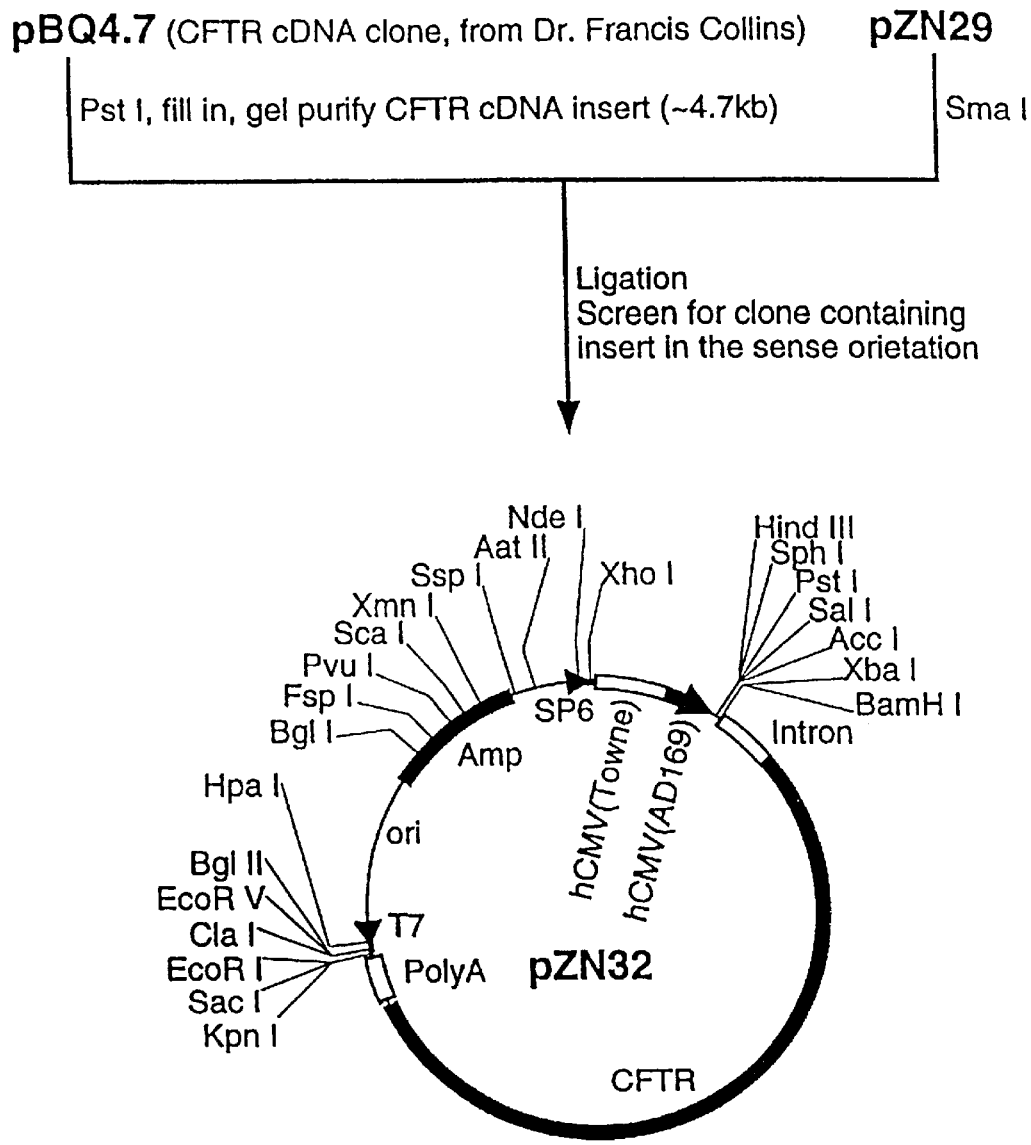
FIG. 5 shows construction of pZN32.

Preparation of plasmid DNA. The plasmid vector used, pZN32, contains the human CFTR gene coding region fused to the human cytomegalovirus immediate early promoter-enhancer element shown in FIGS. 3–5 attached hereto. A fall restriction map of the immediate early enhancer and promoter region of HCMV (Towne) and HCMV (AD169) is provided in FIGS. 6A and 6C. The two sequences are compared in 6B. pZN32 was purified using alkaline lysis and ammonium acetate precipitation, and the nucleic acid concentration measured by UV absorption at 260 nm.

Preparation of cationic liposomes

Liposomes were prepared as small unilamellar vesicles (approximately 100 nm in diameter) containing the cationic lipid DDAB (dimethyl dioctadecyl ammonium bromide) as DDAB cholesterol in a 1:1 molar ratio. DDAB was purchased from Sigma, St. Louis, Mo., and cholesterol was purchased from CalBioChem, San Diego, Calif. Stock solutions of the lipids were dissolved in chloroform. Lipids were mixed in a round-bottomed flask and evaporated to dryness on a rotary evaporator under reduced pressure. Double distilled water was added to produce final lipid concentrations of 10 mM each, and the resulting mix was sonicated for approximately 20 minutes in a bath sonicator (Laboratory Supplies, Hicksville, N.Y.).

Aerosol delivery of plasmid/liposome complexes to mice

Twelve mg of pZN32 complexed to 24 $\mu$mols of DDAB cholesterol liposomes was aerosolized over two different aerosol periods on the same day. To prevent aggregation and precipitation of the oppositely charged components, liposomes and DNA were diluted separately in sterile water prior to mixing. Six mg of plasmid DNA and 12 $\mu$mols of DDAB cholesterol liposomes were each diluted to 8 ml with water and mixed. Equal volumes of the DNA-liposome mixture were then placed into two Acorn I nebulizers (Marquest, Englewood, Colo.), and the animals placed in an Intox small animal exposure chamber (Albuquerque, N.M.). An air flow rate of 4 L min$^{-1}$ was used to generate the aerosol. Ninety minutes were required to aerosolize this volume of 4 ml of DNA-liposome mixture. The animals were removed from the chamber for 1–2 hours and then the above procedure was repeated.

Immunohistochemical staining for the human CFTR protein in mouse lungs

At selected time points following aerosolization, mice were sacrificed and their lungs immediately removed. The lungs were slowly inflated with phosphate buffered saline (PBS) containing 3.3% by volume OCT (Miles, Inc.), then placed in a tissue cassette filled with OCT, and frozen in 2-methylbutane chilled in a dry ice/ethanol bath. Cryosections were cut at 5 $\mu$m and collected onto salinized slides. CFTR protein was detected after fixation of cryosections for 10 minutes in either 4% acetone or 2% paraformaldehyde in PBS containing 0.1% Tween 20 (PBST). All subsequent dilutions and washes were done in PBST. Following fixation, sections were washed three times (5 minutes each) with PBST then covered with 10% normal rabbit serum for 10 minutes at 20° C. Immunolocalization of CFTR was then performed using the affinity purified rabbit polyclonal anti-CFTM antibody, α-1468, provided by Dr. Jonathan Cohn, Duke University. The serum was replaced with α-1468, diluted (1: 1000). The antibody-covered section was gently overlaid with a siliconized coverslip and incubated in a humid chamber at 4° C. for 24 hours. Slides were then warmed to 20° C. and washed three times. The presence of bound rabbit antibody against CFTR was detected by covering sections with biotinylated, affinity purified, goat anti-rabbit antibody (Vector Laboratories), diluted 1:300 for 1 hour, followed by washing (3×10 minutes) and replacement with streptavidin labelled with alkaline phosphatase (Zymed, South San Francisco) for 20 minutes. Immobilized alkaline phosphatase was detected using AP-red (Zymed) as the chromagen, with endogenous alkaline phosphatase being inhibited with levamisole (Zymed). Other controls, run concurrently, included the use of normal rabbit serum in place of primary antibody and the use of lung tissue from untreated mice. Photo-microscopy was performed using Kodak Ektachrome 64T film at X50 and X250.

Results

Photomicrographs of frozen sections (viewed at different magnifications) of mouse lung 48 hours following aerosol exposure to pZN32-DDAB cholesterol liposome complexes and lung from untreated control showed intense staining with the polyclonal anti-CFTR antibody, α-1468, whereas the overwhelming majority of the airways were transfected with the human CFTR gene. Essentially all the cells in transfected airways stain positively, demonstrating that the overwhelming majority of airway cells are transfected with the human CFTR gene in vivo with a single aerosol dose of pZN32 complexed to DDAB-cholesterol liposomes. There was no histologic evidence of lung damage, inflammation or edema present in any of the pZN32-DDAB cholesterol-liposome-treated animals. pZN32-DDAB cholesterol-liposome-treated and control animals could not be distinguished histologically. The expression of the human CFTR gene is present in mouse lungs for at least 60 days following a single aerosol dose of pZN32 complexed to DDAB-cholesterol liposomes. Frozen sections of mouse lungs from control animals did not show any detectable staining for CFTR, confirming that all the CFTR expression present was due to transfection of lung cells with the human CFTR gene.

As shown by the above results, a single aerosol dose of an expression vector, containing a gene of interest, complexed to cationic liposomes transfects the majority of the cells lining both the conducting airways and the alveoli of the lung, the gene product is present in the lung for at least 60 days, the expression appears to be lung-specific, and there is no histological evidence of damage following exposure. There are several potential advantages to using aerosolized cationic liposomes as an in vivo gene delivery system. First, cationic liposomes can mediate efficient transfection of non-dividing cells. This is important because many airway epithelial cells are well differentiated and divide slowly or not at all. Second, liposomes (including liposomes containing cationic lipids) are non-infectious, and appear to be both well tolerated and non-immunogenic in a variety of human clinical trials. The effects of repeated aerosol administration of DNA/liposome complexes is effective and is non-toxic. More precise intrapulmonary targeting may be achieved by a) altering aerosol particle size to preferentially direct the aerosol to alveoli or proximal versus distal airways or b) to covalently couple monoclonal antibodies to the liposome surface, thereby targeting lung cells expressing the corresponding cell surface antigen. Cationic liposome-mediated DNA delivery by aerosol provides high level, lung-specific transgene expression in vivo.

All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of making an aerosolized lipid-nucleic acid complex composition, comprising:
   mixing a cationic liposome and a selected nucleic acid to form a cationic lipid-nucleic acid complex, which complex does not substantially aggregate in vitro; and,
   aerosolizing the cationic lipid-nucleic acid complex to provide an aerosolized complex.

2. The method of claim 1, further comprising suspending the liposome and the nucleic acid, each in aqueous solutions, prior to mixing.

3. The method of claim 1, further comprising separately diluting the liposome or the nucleic acid prior to mixing in an aqueous buffer.

4. The method of claim 1, comprising diluting the cationic lipid nucleic acid complex in a physiologically acceptable diluent prior to aerosolization.

5. The method of claim 4, comprising diluting the cationic lipid nucleic acid complex in a physiologically acceptable diluent selected from deionized water, and 5% dextrose in water.

6. The method of claim 1, comprising diluting the cationic lipid nucleic acid complex in a physiologically acceptable diluent comprising a stabilizer or biocide.

7. The method of claim 1, further comprising measuring the mean particle size of the aerosolized complex.

8. The method of claim 1, wherein mean particle size of the complex is less than 15 μm after aerosolization.

9. The method of claim 1, wherein mean particle size of the complex is less than 5 μm after aerosolization.

10. The method of claim 1, wherein mean particle size of the complex is about 0.2 to 4 μm after aerosolization.

11. The method of claim 1, wherein mean particle size of the complex is between about 5 μm and about 10 μm after aerosolization.

12. The method of claim 1, further comprising packaging the cationic lipid-nucleic acid complex in a container prior to aerosolization.

13. The method of claim 1, further comprising packaging the cationic lipid-nucleic acid complex prior to aerosolization, wherein the cationic lipid-nucleic acid complex is packaged in a sterile container comprising one or more unit dose of the complex.

14. The method of claim 1, wherein the cationic lipid-nucleic acid complex is aerosolized by nebulizing the complex in a nebulizer.

15. The method of claim 1, further comprising nebulizing the cationic lipid-nucleic acid complex in a nebulizer and administering the aerosolized complex through a mouthpiece or facemask.

16. The method of claim 1, wherein the nucleic acid is a DNA and the concentration of DNA in the composition is less than 5 mg DNA/ 8 ml of composition.

17. The method of claim 1, wherein the composition does not comprise a chelating agent.

18. The method of claim 1, wherein the composition is a low-salt mixture.

19. The method of claim 1, wherein the liposome and nucleic acid are mixed by agitation.

20. The method of claim 1, wherein the liposome is prepared by mixing constituent lipids of the liposome in chloroform, followed by evaporation of the chloroform and resuspension of the liposome in an aqueous solution.

21. The method of claim 1, wherein the liposome is prepared by drying a composition comprising the lipid components of the liposome, adding an aqueous solution to the resulting dried lipid components, and vortexing or sonicating the aqueous solution added to the dried lipid components to produce liposomes.

22. The method of claim 19, further comprising extruding the resulting liposomes through a polycarbonate membrane.

23. The method of claim 1, wherein the cationic liposome comprises a non-cationic lipid.

24. The method of claim 1, wherein the cationic liposome comprises cholesterol.

25. The method of claim 1, wherein the cationic liposome is a small unilamellar vesicle (SUV).

26. The method of claim 1, wherein the cationic liposome is a multilamellar vesicle (MLV).

27. The method of claim 1, wherein the cationic liposome is a large unilamellar vesicle (LUV).

28. The method of claim 1, wherein the cationic liposome is mixed with the nucleic acid at a ratio of about 4:1 to about 1:10 micrograms nucleic acid to nanomoles cationic lipid.

29. The method of claim 1, wherein the cationic liposome is mixed with the nucleic acid at a ratio of about 1:1 to about 1:2 micrograms nucleic acid to nanomoles cationic lipid.

30. The method of claim 1, wherein the cationic liposome is between about 100 nm and 10 microns in diameter.

31. The method of claim 1, wherein the cationic liposome is between about 100 nm and 500 nm in diameter.

32. The method of claim 1, wherein the selected nucleic acid comprises DNA.

33. The method of claim 1, wherein the selected nucleic acid encodes a detectable or selectable marker.

34. The method of claim 1, wherein the selected nucleic acid encodes the human CFTR protein.

35. The method of claim 1, wherein the selected nucleic acid encodes the human CFTR protein, which protein is expressed under the control of the HCMV immediate early enhancer and promoter.

36. The method of claim 1, wherein the selected nucleic acid encodes one or more of: a toxic peptide, a tumor suppressor, an anti-sense molecule, an anti-bacterial agent, and a cytokine.

37. The method of claim 1, wherein the cationic lipid-nucleic acid complex comprises a targeting agent.

38. The method of claim 1, wherein the nucleic acid comprises a plasmid.

* * * * *

```
                              SEQUENCE LISTING (1) GENERAL INFORMATION:

(iii) NUMBER OF SEQUENCES:         4

(2) INFORMATION FOR SEQ ID NO:    1:

(i) SEQUENCE CHARACTERISTICS:
          (A) LENGTH:                  616
          (B) TYPE:                    nucleic acid
          (C) STRANDEDNESS:            single
          (D) TOPOLOGY:                linear (xi) SEQUENCE DESCRIPTION: SEQ ID NO: 1:

GGCGACCGCC CAGCGACCCC CGCCCGTTGA CGTCAATAGT GACGTATGTT CCCATAGTAA     60

CGCCAATAGG GACTTTCCAT TGACGTCAAT GGGTGGAGTA TTTACGGTAA ACTGCCTACT    120

TGGCAGTACA TCAAGTGTAT CATATGCCAA GTCCGCCCCC TATTGACGTC AATGACGGTA    180

AATGGCCCGC CTAGCATTAT GCCCAGTACA TGACCTTACG GGAGTTTCCT ACTTGGCAGT    240

ACATCTACGT ATTAGTCATC GCTATTACCA TGGTGATGCG GTTTTGGCAG TACACCAATG    300

GGCGTGGATA GCGGTTTGAC TCACGGGGAT TTCCAAGTCT CCACCCCATT GACGTCAATG    360

GGAGTTTGTT TTGGCACCAA AATCAACGGG ACTTTCCAAA ATGTCGTAAT AACCCCGCCC    420

CGTTGACGCA AATGGGCGGT AGGCGTGTAC GGTGGGAGGT CTATATAGCA GAGCTCGTTT    480

AGTGAACCGT CAGATCGCCT GGAGACGCCA TCCACGCTGT TTTGACCTCC ATAGAAGACA    540

CCGGGACCGA TCCAGCCTCC GCGGCCGGGA ACGGTGCATT GGAACGCGGA TTCCCCGTGC    600

CAAGAGTGAC GTAAGT                                                    616

(2) INFORMATION FOR SEQ ID NO:    2:

(i) SEQUENCE CHARACTERISTICS:
          (A) LENGTH:                  930
          (B) TYPE:                    nucleic acid
          (C) STRANDEDNESS:            single
          (D) TOPOLOGY:                linear (xi) SEQUENCE DESCRIPTION: SEQ ID NO: 2:

AATCAATATT GGCCATTAGC CATATTATTC ATTGGTTATA TAGCATAAAT CAATATTGGC     60

TATTGGCCAT TGCATACGTT GTATCCATAT CATAATATGT ACATTTATAT TGGCTCATGT    120

CCAACATTAC CGCCATGTTG ACATTGATTA TTGACTAGTT ATTAATAGTA ATCAATTACG    180

GGGTCATTAG TTCATAGCCC ATATATGGAG TTCCGCGTTA CATAACTTAC GGTAAATGGC    240

CCGCCTGGCT GACCGCCCAA CGACCCCCGC CCATTGACGT CAATAATGAC GTATGTTCCC    300

ATAGTAACGC CAATAGGGAC TTTCCATTGA CGTCAATGGG TGGAGTATTT ACGGTAAACT    360

GCCCACTTGG CAGTACATCA AGTGTATCAT ATGCCAAGTA CGCCCCCTAT TGACGTCAAT    420
```

```
GACGGTAAAT GGCCCGCCTG GCATTATGCC CAGTACATGA CCTTATGGGA CTTTCCTACT    480

TGGCAGTACA TCTACGTATT AGTCATCGCT ATTACCATGG TGATGCGGTT TTGGCAGTAC    540

ATCAATGGGC GTGGATAGCG GTTTGACTCA CGGGGATTTC CAAGTCTCCA CCCCATTGAC    600

GTCAATGGGA GTTTGTTTTG CACCAAAAT CAACGGGACT TTCCAAAATG TCGTAACAAC     660

TCCGCCCCAT TGACGCAAAT GGGCGGTAGG CGTGTACGGT GGGAGGTCTA TATAAGCAGA    720

GCTCGTTTAG TGAACCGTCA GATCGCCTGG AGACGCCATC CACGCTGTTT TGACCTCCAT    780

AGAAGACACC GGGACCGATC CAGCCTCCGC GGCCGGGAAC GGTGCATTGG AACGCGGATT    840

CCCCGTGCCA AGAGTGACGT AAGTACCGCC TATAGAGTCT ATAGGCCCAC CCCCTTGGCT    900

TCTTATGCAT GCTATACTGT TTTTGGCTTG                                    930

(2) INFORMATION FOR SEQ ID NO:    3:

(i) SEQUENCE CHARACTERISTICS:
        (A) LENGTH:          616
        (B) TYPE:            nucleic acid
        (C) STRANDEDNESS:    single
        (D) TOPOLOGY:        linear (xi) SEQUENCE DESCRIPTION: SEQ ID NO: 3:

GGCGACCGCC CAGCGACCCC CGCCCGTTGA CGTCAATAGT GACGTATGTT CCCATAGTAA     60

CGCCAATAGG GACTTTCCAT TGACGTCAAT GGGTGGAGTA TTTACGGTAA ACTGCCCACT    120

TGGCAGTACA TCAAGTGTAT CATATGCCAA GTCCGCCCCC TATTGACGTC AATGACGGTA    180

AATGGCCCGC CTAGCATTAT GCCCAGTACA TGACCTTACG GGAGTTTCCT ACTTGGCAGT    240

ACATCTACGT ATTAGTCATC GCTATTACCA TGGTGATGCG GTTTTGGCAG TACACCAATG    300

GGCGTGGATA GCGGTTTGAC TCACGGGGAT TTCCAAGTCT CCACCCCATT GACGTCAATG    360

GGAGTTTGTT TTGGCACCAA AATCAACGGG ACTTTCCAAA ATGTCGTAAT AACCCCGCCC    420

CGTTGACGCA AATGGGCGGT AGGCGTGTAC GGTGGGAGGT CTATATAGCA GAGCTCGTTT    480

AGTGAACCGT CAGATCGCCT GGAGACGCCA TCCACGCTGT TTTGACCTCC ATAGAAGACA    540

CCGGGACCGA TCCAGCCTCC GCGGCCGGGA ACGGTGCATT GGAACGCGGA TTCCCCGTGC    600

CAAGAGTGAC GTAAGT                                                   616

(2) INFORMATION FOR SEQ ID NO:    4:

(i) SEQUENCE CHARACTERISTICS:
        (A) LENGTH:          930
        (B) TYPE:            nucleic acid
        (C) STRANDEDNESS:    single
        (D) TOPOLOGY:        linear (xi) SEQUENCE DESCRIPTION: SEQ ID NO: 4:

AATCAATATT GGCCATTAGC CATATTATTC ATTGGTTATA TAGCATAAAT CAATATTGGC     60

TATTGGCCAT TGCATACGTT GTATCCATAT CATAATATGT ACATTTATAT TGGCTCATGT    120

CCAACATTAC CGCCATGTTG ACATTGATTA TTGACTAGTT ATTAATAGTA ATCAATTACG    180

GGGTCATTAG TTCATAGCCC ATATATGGAG TTCCGCGTTA CATAACTTAC GGTAAATGGC    240

CCGCCTGGCT GACCGCCCAA CGACCCCCGC CCATTGACGT CAATAATGAC GTATGTTCCC    300

ATAGTAACGC CAATAGGGAC TTTCCATTGA CGTCAATGGG TGGAGTATTT ACGGTAAACT    360

GCCCACTTGG CAGTACATCA AGTGTATCAT ATGCCAAGTA CGCCCCCTAT TGACGTCAAT    420

GACGGTAAAT GGCCCGCCTG GCATTATGCC CAGTACATGA CCTTATGGGA CTTTCCTACT    480

TGGCAGTACA TCTACGTATT AGTCATCGCT ATTACCATGG TGATGCGGTT TTGGCAGTAC    540
```

-continued

```
ATCAATGGGC GTGGATAGCG GTTTGACTCA CGGGGATTTC CAAGTCTCCA CCCCATTGAC      600

GTCAATGGGA GTTTGTTTTG GCACCAAAAT CAACGGGACT TTCCAAAATG TCGTAACAAC      660

TCCGCCCCAT TGACGCAAAT GGGCGGTAGG CGTGTACGGT GGGAGGTCTA TATAAGCAGA      720

GCTCGTTTAG TGAACCGTCA GATCGCCTGG AGACGCCATC CACGCTGTTT TGACCTCCAT      780

AGAAGACACC GGGACCGATC CAGCCTCCGC GGCCGGGAAC GGTGCATTGG AACGCGGATT      840

CCCCGTGCCA AGAGTGACGT AAGTACCGCC TATAGAGTCT ATAGGCCCAC CCCCTTGGCT      900

TCTTATGCAT GCTATACTGT TTTTGGCTTG                                       930
```